US005834188A

United States Patent [19]
Harada et al.

[11] Patent Number: 5,834,188
[45] Date of Patent: Nov. 10, 1998

[54] METHODS AND COMPOSITIONS FOR IDENTIFYING MORPHOGEN ANALOGS

[75] Inventors: Shun-ichi Harada, North Wales, Pa.; Kuber T. Sampath, Medway, Mass.; Gideon A. Rodan, Bryn Mawr, Pa.

[73] Assignee: Creative BioMolecule, Inc., Hopkinton, Mass.

[21] Appl. No.: 507,598

[22] Filed: Jul. 26, 1995

[51] Int. Cl.$^6$ .............................. C12N 5/00; C12Q 1/02; C12Q 1/68
[52] U.S. Cl. .................... 435/6; 435/4; 435/325; 536/24.1
[58] Field of Search .............................. 435/320.1, 240.2, 435/4, 325, 6; 536/23.1, 23.2, 24.1

[56] References Cited

U.S. PATENT DOCUMENTS 5,665,543  9/1997  Foulkes et al. .............................. 435/6

FOREIGN PATENT DOCUMENTS

| WO 95/11983 | 5/1995 | WIPO . |
| WO 95/14104 | 5/1995 | WIPO . |
| WO 95/33831 | 12/1995 | WIPO . |
| WO 96/38590 | 12/1996 | WIPO . |
| WO 97/05241 | 2/1997 | WIPO . |
| WO 97/05284 | 2/1997 | WIPO . |

OTHER PUBLICATIONS

Orkin, et al. (1995) Report and Recommendations of the Panel to Assess the NIH Investment in Research on Gene Theraphy.
LuValle, et al. (1993) Journal of Cell Biology, vol. 121 No. 5 pp. 1173–1179.
Elima, et al. (1993) Biochem. Journal. vol. 289 pp. 247–253.
Knutsen, et al. (1993) Biochemical and Biophysical Research Communications vol. 194, No. 3 pp. 1352–1358.
Wilkins, BioEssays 17(5):375–377 (1995).
Lee et al. (1987), "Purified Transcription Factor AP–1 Interacts with TPA–Inducible Enhancer Elements," 49 *Cell* 741–752.
Ohta et al. (1992), "Bone Morphogenetic Proteins (BMP–2 and BMP–3) Induce the Late Phase Expression of the Proto–Oncogene c–fos in Murine Osteoblastic MC3T3–E1 Cells," 314 *FEBS* 3:356–360.
Wang et al. (1992), "Bone and Haematopoietic Defects in Mice Lacking c–fos," 360 *Nature* 741–745.
Asahina et al. (1993), "Human Osteogenic Protein–1 Induces Both Chondroblastic and Osteoblastic Differentiation of Osteoprogenitor Cells Derived From Newborn Rata Calvaria," 123 *J. Cell Biol.* 4:921–933.
Chen et al. (1993), "Bovine Articular Chondrocytes Do Not Undergo Hypertrophy When Cultured In the Presence of Serum and Osteogenic Protein–1," 197 *Biochem. & Biophys. Res. Commun.* 3:1253–1259.
Elima et al. (1993), "The Mouse Collagen X Gene: Complete Nucleotide Sequence, Exon Structure and Expression Pattern," 289 *Biochem. J.* 247–253.

Lovell et al. (1993), "Bone Morphogenetic Proteins Increase Type X Collagen Synthesis in vivo," *J. Cell. Biochem.* Abstract No. 17E:166.
Michiels et al. (1993), "Retroviruses and Oncogenes Associated With Osteosarcomas," *Osteosarcoma In Adolescents and Young Adults* G. Bennett Humphrey (ed.), Kluwer Academic Publishers, Boston, MA.
Liu et al. (1994), "Simultaneous Detection of Multiple Bone–Related mRNAs and Protein Expresion During Osteoblast Differentiation: Polymerase Chain Reaction and Immunocytochemical Studies At The Single Cell Level," 166 *Dev. Biol.* 220–234.
Rosen et al. (1994), "Responsiveness of Clonal Limb Bud Cell Lines to Bone Morphogenetic Protein 2 Reveals a Sequential Relationship Between Cartilage and Bone Cell Phenotypes," 9 *J. Bone & Min. Res.* 1759–1768.
Strong et al. (1994), "The Effects of the Insulin–Like Growth Factors and Transforming Growth Factor β on the Jun Proto–Oncogene Family in MC3T3–E1 Cells," 55 *Calcif. Tissue Int.* 311–315.
Carey et al. (1995), "Expression of Bone Morphogenetic Protein–6 Messenger RNA in Bovine Growth Plate Chondrocytes of Different Size," 10 *J. Bone & Min. Res.* 3:401–405.
Chen et al. (1995), "Osteogenic Protein–1 Promotes Growth and Maturation of Chick Sternal Chondrocytes in Serum–Free Cultures," 108 *J. Cell Sci.* 105–114.
Sassone–Corsi (1995), "Signaling Pathways and c–fos Transcriptional Response—Links to Inherited Diseases," 332 *N.E. J. Med.* 23:1576–1577.
Harada et al. (1995), "Induction of Vascular Endothelial Growth Factor by Osteogenic Protein 1 in vitro and in vivo," 10 *Am. Soc. Bone & Min. Res.* Suppl. 1, Abstract No. T268.
Harada et al. (1995), "Osteogenic Protein 1 Stimulates Type X Collagen Promoter Via A Fos Family Protein," 10 *Am. Soc. Bone & Min. Res.* Suppl. 1, Abstract No. T345.
Vainio et al. (1993), "Identification of BMP–4 as a Signal Mediating Secondary Induction Between Epithelial and Mesenchymal Tissues During Early Tooth Development," 75 *Cell* 45–58.
Harada et al. (1995), "Characterization of the Osteogenic Protein–1 Response Element in the Type X Collagen Promoter," 6 *Mol. Biology of the Cell.* Suppl., p. 393a, Abstract No. 2284.

(List continued on next page.)

*Primary Examiner*—Johnny F. Railey, II
*Attorney, Agent, or Firm*—Testa, Hurwitz & Thibeault LLP

[57] ABSTRACT

Disclosed herein are methods and compositions for identifying morphogen analogs. Preferred methods rest on the use of test cells comprising DNA defining a morphogen-responsive transcription activating element operatively associated with a reporter gene. In certain embodiments, the methods involve an osteogenic protein 1 (OP-1) responsive transcription activating element. Substances that activate the OP-1 responsive transcription activating element are considered herein likely to be useful for reproducing in vivo effects of morphogens such as OP-1.

10 Claims, 12 Drawing Sheets

OTHER PUBLICATIONS

Elima et al. (1993), "The Mouse Collagen X Gene: Complete Nucleotide Sequence, Exon Structure and Expression Pattern," 289 *Biochem. J.* 1:247–253.

Maliakal et al. (1994), "Osteogenic Protein–1 (BMP–7) Inhibits Cell Proliferation and Stimulates the Expression of Markers Charactertistic of Osteoblast Phenotype In Rat Osteosarcoma (17/2.8) Cells," 11 *Growth Factors* 3:227–234.

Harada et al. (1995), "Identification of An AP1–Like Response Region For Osteogenic Protein–1 In Type X Collagen Promoter," *Annals of The New York Academy of Science, No. 785,* Molecular and Developmental Biology of Cartilage Conference, Bethesda, Maryland, USA, Sep. 27–30, 1995.

Harada et al. (1995), "Characterization of the Osteogenic Protein–1 Response Element In The Type X Collagen Promoter," Thirty–Fifth Annual Meeting of the American Society For Cell Biology, Washington, D.C., Dec. 9–13, 1995, *Molecular Biology of the Cell* 6 (Suppl.) 393A.

Harada et al. (1996), "Characterization of the Osteogenic Protein–1 Response Region In The Type X Collagen Promoter," Sixth Workshop On Cells and Cytokines In Bone and Cartilage, Davos, Switzerland, Jan. 7–10, 1996, 17 *Bone* (New York)6:124.

Harada et al. "Osteogenic Protein–1 Upregulation of the Mouse Collagen X Promoter Activity is Mediated by a MEF–2 Like Sequence and Requires an Adjacent AP–1 Sequence", 2nd International Conference of Bone Morphogenetic Proteins, Sacramento, CA, Jun. 4–8, 1997.

Ghosh–Choudhury et al. "Immortalized Murine Osteoblasts Derived from BMP 2–T–Antigen Expressing Transgenic Mice", *Endocrinology,* 137:331–339 (1997).

Harris et al., "Recombinant Bone Morphogenetic Protein 2 Accelerates Bone Cell Differentiation and Stimulates BMP–2 mRNA Expression and BMP–2 Promoter Activity in Primary Fetal Rat Calvarial Osteoblast Cultures" *Molecular and Cellular Differentiation* 3:137–155 (1995).

Harada et al. (1995), "Characterization of the Osteogenic Protein–1 Response Region In The Type X Collagen Promoter," Abstract 124 *Bone* 17(6):590.

Harada et al. (1995), "Identification of an AP1 Like Response Region For Osteogenic Protein–1 In Type X Collagen Promoter," Abstract Distributed at New York Academy Science, Molecular and Developmental Biology of Cartilage, Sep. 27–30, 1995.

EFFECT OF OP1 (300 ng/ml) ON OSTEOBLAST MARKERS IN C5.18 CELLS

COL 1α(1) ←
← 28S
← 18S

ALP ←
← 28S
← 18S

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1067 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..1067
        ( D ) OTHER INFORMATION: /product="MOUSE TYPE 10 COLLAGEN PROMOTER"

( x i ) SEQUENCE DESCRIPTION: SEQ ID NO:1:

```
TCGATCCTAA AACACTTAAG GATATTTCTG TAAGGCTGTG AAAGAGAAAA CCAACTACTT      60
ACACGGATGG AGACCATGTT TATTTCTTTG GGAGAAAAGC CTAATTGGGA CGCTTCGAGA     120
TCCCTATAGG AAATTGCACC AGTAGTCAAC TGGATTTTTA AAAGGCAAAG CTTGAGGATT     180
TTTTTTTCCC TTTGAAATGA ATGTAGCAAA CTTATGTAAG CACGGAATAG GATTATTAGT     240
TAACAGTCTT TTCAATTATA TGGGAAAATG AAAACTAGGG GAGCGTCTAA GGCCACTTGC     300
TGACCTTTGT GCAGCTGTTA AGTAAAGAAA GTAAACCCTC CAGGGATACT GAACAGCCAA     360
CTGTCATAAG TCCAGGGTGT CTTGCACTTG CTGTGACAAG TTTAAAATAT TTAATATGAC     420
TATACCTGAA ATATTTAATG CTATCTTTTT CATGCACCAG CTTCTAAGAG CTTTCCCTAA     480
AATCCTGATA TGCAAAAGAA TATACCAATA TTTTCCCCCT TGCCCTGGC GCTTGTCTCC      540
CAAGTTAGCA AACACTTAGG TAAGCGATTT TTACAGAACT TTTTCCCTA ATAACTGAAG      600
GACTAACATG ATGATTTAGA TCTATATTCT CCCCAAAAGG CGTCTCATAT TTTTGTATAT     660
TACCAAATAT TTTCAGTCAA ATAACACAAG AATGTATTTT AAAAATAAAA AGGGTGAATC     720
ATCATTCCAT CATGAACCAA CATTGGACTC AGAACTCCTA AAAGGAAAAC AGAAAAAAAA     780
AAAAAATCAT GCACAGCCGA AGCTATTAAT ATATAATGGA GACAAAGAGT TTATTTTTCA     840
ATGAGAATAA CAAGGAAAAA AGCCTGATTT TGTACGCCTG CCCGTTAGGA CTTCCCACCA     900
TAATTAGTGC TTCTTGCCCC TGAGAGGAGG AGCTTCGGCT CAGGGGAACT TCATGCAATA     960
AGGGAAGAAA ACAGTATAAA TACTCCAGGG CAGCCGTGGG GAAGGCATTA TCCACTGCTC    1020
CTGGGCAGAG GAAGCCAGGA AAGCTGCCCC ACGCATCTCC CAGCACC                 1067
```

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..21
        ( D ) OTHER INFORMATION: /product="AP1 SEQUENCE"

( x i ) SEQUENCE DESCRIPTION: SEQ ID NO:2:

CGCTTGATGA CTCAGCCGGA A						21

(2) INFORMATION FOR SEQ ID NO:3:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..10
        (D) OTHER INFORMATION: /product="AP1 MUTATION"

(xi) SEQUENCE DESCRIPTION: SEQ ID NO:3:

TTCCTCATCA						10

(2) INFORMATION FOR SEQ ID NO:4:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..25
        (D) OTHER INFORMATION: /note= "Conserved domain of human
            c-fos"

(xi) SEQUENCE DESCRIPTION: SEQ ID NO:4:

Lys Val Glu Gln Leu Ser Pro Glu Glu Glu Glu Lys Arg Arg Ile Arg
1               5                   10                  15

Arg Ile Arg Asn Lys Met Ala Ala Ala
            20                  25

METHODS AND COMPOSITIONS FOR IDENTIFYING MORPHOGEN ANALOGS

FIELD OF THE INVENTION

The present invention relates generally to methods and compositions for screening and identifying substances useful as morphogen analogs. In certain embodiments, the identified substances can be used to mimic a biological effect of osteogenic protein 1 (OP-1) on cellular gene expression and/or tissue-specific morphogenesis in mammals.

BACKGROUND OF THE INVENTION

Osteogenic Protein-1 of human origin (hOP-1), described in U.S. Pat. Nos. 5,011,691 and 5,266,683, and in Ozkaynak et al. (1990) *EMBO J.* 9: 2085–2093, recently has been appreciated to be competent to induce genuine tissue morphogenesis in mammals, including the endochondral morphogenesis of bone. It has further been appreciated that mouse OP-1 (see U.S. Pat. No. 5,266,683) and the Drosophila melanogaster gene product 60A, described in Wharton et al. (1991) *Proc. Natl. Acad. Sci. USA* 88:9214–9218 similarly induce true tissue morphogenesis in mammals. Related proteins, including OP-2 (Ozkaynak (1992) J. Biol. Chem. 267:25220–25227 and U.S. Pat. No. 5,266,683); BMP5, BMP6 (Celeste et al. (1991) Proc. Natl. Acad. Sci. USA 87:9843–9847, Vgr-1 (Lyons et al. (1989) Proc. Natl. Acad. Sci. USA 86:4554–4558), and the like are similarly believed to be competent to induce true morphogenesis of mammalian tissue. As a result, significant effort has been devoted to characterizing and developing these and other functionally and structurally related proteins (collectively, morphogens) for use in the regenerative healing of injured or diseased mammalian tissues or organs. Particular effort has been devoted to developing morphogen-based therapeutics for the treatment of injured or diseased mammalian bone tissue, including for example, therapeutic compositions for inducing regenerative healing of bone defects such as fractures, as well as for preserving or restoring healthy metabolic properties in diseased bone tissue, e.g., osteopenic bone tissue. Complete descriptions of efforts to develop and characterize morphogen-based therapeutics for use in mammals, including humans, are set forth in pending U.S. patent application Nos. 08/404,113, 08/396,930, 08/445, 467, 08/152,901, 08/432,883, 08/155,343, 08/260,675, 08/165,541, 08/174,605 and 07/971,091, the teachings of each of which are incorporated herein by reference.

Certain complications, however, presently are encountered during the production, formulation and use in vivo of therapeutic macromolecules, such as morphogen proteins. For example, such proteins are typically produced by fermentation or culture of suitable host cells. Any biological product produced from such host cells for use in humans presently must be shown to be essentially free of host cell contaminants, such as secreted or shed proteins, viral particles or degradation products thereof. Providing such assurance can add significantly to the cost and technical difficulty of commercial production of biological macromolecules. Furthermore, appropriate formulations must be developed for conferring commercially reasonable shelf life on the produced macromolecule, without significant loss of biological efficacy. An additional complicating factor arises when circumstances warrant an extended course of therapeutic treatment with the produced and formulated macromolecule: the treated mammal may develop an immunological response to the macromolecule, and any such response may interfere with effectiveness thereof. In extreme circumstances, treatment must be discontinued.

Accordingly, needs remain for the identification of therapeutically effective analogs of the aforesaid morphogens, particularly for analogs that are inexpensive to produce, are robust upon storage, and have a reduced propensity for eliciting undesirable side effects upon chronic or repeated administration to a mammal.

It is an object of the invention described herein to provide methods and compositions for identifying a morphogen analog, that is, for identifying a substance that mimics a morphogen biological effect in living cells or tissue. It is a further object of the present invention to provide an analog identified according to the present identification method. It is yet a further object to provide a therapeutic composition comprising an identified analog suitable for administration to a mammal in need thereof, such as a mammal afflicted with a metabolic bone disease, e.g., a disease characterized by osteopenia.

SUMMARY OF THE INVENTION

The present invention provides methods and compositions for identifying morphogen analogs. A morphogen analog of the present invention is a substance, preferably suitable for administration to a mammal in need thereof, that can induce a morphogen-mediated biological effect. That is, the analog of the present invention can reproduce a biological effect naturally induced in living mammalian cells or tissue by a morphogen. As used herein, the term "morphogen" embraces the class of proteins typified by human osteogenic protein 1 (hOP-1). hOP-1 and functionally equivalent morphogens are dimeric proteins that induce uncommitted cells of mammalian origin to undergo a cascade of cellular and molecular events that culminates in the formation of functional, differentiated mammalian tissues, e.g., bone, liver, nerve, tooth dentin, periodontal tissue, gastrointestinal tract lining tissue and the like. As described herein, morphogen analogs are identified by assessing whether candidate substances can mimic the morphogen OP-1 by inducing OP-1 mediated expression of a reporter gene and/or by inducing an OP-1 mediated biological effect. The present invention embraces substances identified according to the methods set forth herein as morphogen analogs. Further, the present invention provides for the production of commercially significant quantities of identified morphogen analogs. Still further, the invention provides for the manufacture and use of DNA comprising a morphogen-responsive transcription activating element. The present DNA can be used to render the expression of a gene of interest, e.g., a reporter gene encoding a detectable gene product, inducible by OP-1 or a functionally equivalent morphogen or analog thereof. Yet further, the present DNA can be used in the manufacture of a cell for the in vitro or in vivo OP-1 or analog inducible expression of a gene product of interest.

Accordingly, in one aspect, the instant invention features an identification method in which a test cell is exposed to at least one candidate substance suspected of having activity as a morphogen analog. The test cell comprises DNA defining an OP-1 responsive transcription activating element, and, in operative association therewith, a reporter gene encoding a detectable gene product Thus, when the DNA is present in an OP-1 responsive cell (e.g., a cell that displays an OP-1 receptor), the DNA serves to induce transcription of the reporter gene when the OP-1 responsive cell is exposed to OP-1. The present method further comprises the step of detecting expression of the detectable gene product following exposure of the test cell to the candidate substance. Expression of the detectable gene product indicates that the candidate substance is competent to induce an OP-1 mediated biological effect. An OP-1 mediated biological effect of particular interest herein comprises the transcriptional activation of OP-1 responsive genes, that is, genes with which the present activating element is naturally in operative association.

In certain embodiments, the present method further comprises the steps of contacting an OP-1 responsive cell with a putative morphogen analog identified as described above and detecting whether the analog can induce a biological effect known to be mediated naturally by OP-1 in the OP-1 responsive cell. If desired, this confirming step can be carried out concurrently with the initial identification steps. In certain specific embodiments, the test cell is an OP-1 responsive cell.

In other embodiments, the present method further comprises the steps of administering the putative morphogen analog identified as described above to a morphogenically permissive, tissue-specific locus in a mammal and detecting whether the analog can induce tissue-specific morphogenesis at the locus. This confirming step advantageously indicates whether the analog will induce tissue-specific morphogenesis in vivo.

In a related aspect, the present invention provides a substantially pure substance competent to bind to at least a portion of the above-mentioned OP-1 responsive transcription activating element, such that the substance, when so bound, modulates expression of a gene in operative association with the aforesaid transcription activating element. This substance is referred to herein as an "expression activator". It will be appreciated that the present invention provides a method for assessing whether a sample such as a cell-free lysate or extract of biological origin, comprises an expression activator. In this method, the sample is contacted with the above-described DNA, and binding of the expression activator to the DNA is subsequently detected according to known methods. This identification method can be routinely adapted for use as an affinity purification method to obtain purified preparations of the expression activator. It is believed that the expression activator may be a novel intracellular protein, e.g., a member of the fos family of DNA binding proteins.

As a result of the present analog identification method, the invention provides for the production of therapeutic-grade commercially significant quantities of an identified morphogen analog. The invention further provides for production of a derivative of the morphogen analog in which any undesirable properties of the initially-identified analog, such as in vivo toxicity or tendency to degrade upon storage, are mitigated. Thus, a morphogen analog or functionally equivalent derivative thereof can be formulated in a therapeutic composition suitable for administration to a mammal in need thereof. Preferably, the therapeutic composition is suitable for administration to a primate, such as a human. Mammals in need of the morphogen analog identified according to teachings set forth herein can be afflicted with any disease or condition for which elicitation of a morphogenic biological effect will provide an improvement in the mammals' health or clinical status, including the stabilization of a deteriorative condition. For example, the mammal can be afflicted with a metabolic bone disease, e.g., a disease characterized by osteopenia. OP-1 and related morphogens are anticipated to beneficially alter the metabolic balance of osteopenic bone tissue such that the metabolic properties of healthy adult bone tissue are restored therein. Alternatively the mammal can be afflicted with ischemic, ulcerative or inflammatory tissue damage, or with injury or deterioration of a morphogen-responsive tissue such as bone, liver, nerve, gastrointestinal tract lining, tooth dentin, periodontal tissue and the like. Further, the therapeutic composition can be suitable for the treatment or preservation ex vivo of mammalian tissue or cells, e.g., for purposes of organ or tissue transplantation.

Another aspect of the present invention provides a cell for the inducible expression of a morphogen. The cell comprises a first DNA encoding the morphogen and a second DNA in transcriptionally operative association therewith and comprising the above-described OP-1 responsive transcription activating element. The cell further comprises cellular means for producing an intracellular substance that binds with the second DNA so as to stimulate expression of the morphogen encoded by the first when the cell is contacted with an extracellular inducing agent. Thus, for example, the cell comprises means for producing an intracellular expression activator of the present invention. Of course, according to the inventive principles set forth herein, the cell of the present invention can comprise a first DNA encoding any desired gene product, the expression of which is advantageously induced by a morphogen, particularly OP-1, or by a morphogen analog of the present invention. In certain embodiments, the first DNA comprises a reporter gene encoding a detectable gene product. Cells comprising such a first DNA are suitable for use in the above-described method for identifying morphogen analogs.

In other embodiments, the first DNA comprises a gene encoding a gene product having biological activity, e.g., an enzyme, growth factor, lymphokine, cytokine, blood or serum protein, clotting factor, or the like. Thus, the first DNA can encode a polypeptide naturally produced by kidney, bone, liver, nerve, pancreatic, adrenal or other mammalian body tissue. Cells comprising such a first DNA are suitable for the inducible production, either in vitro or in vivo, of the biologically active encoded gene product.

Accordingly, in another aspect, the invention provides methods for inducing expression, including autocrine expression, of a gene product such as a morphogen encoded by said first DNA. The present methods involve providing one of the above-described cells and contacting the cell with an extracellular inducing agent, such as OP-1, or an analog thereof, under conditions sufficient to induce expression of the gene present in said first DNA. The induced expression is referred to herein as autocrine expression when the extracellular inducing agent is the same substance as that encoded by the first DNA, such that an initial dose of the extracellular inducing agent triggers sustained expression of the first DNA in a manner similar to naturally occurring autocrine expression or positive feedback expression in biological systems. Certain embodiments of the present invention further involve the additional step of providing the above-described cell to a mammal for in vivo production of the product encoded by the first DNA. Advantageously, the above-described contacting step can be carried out by administering the extracellular inducing agent to the mammal in whom the cell is implanted. The present invention accordingly provides novel methods for administering a morphogen or another gene product having biological activity, to a mammal in need thereof. The present methods offer particular advantages where the mammal has a long-term need for the morphogen or other gene product, e.g. wherein the mammal has a metabolic bone disease, such as for example osteopenia. Alternatively, the present methods offer advantages where the mammal suffers from a clinically acute loss of natural tissue function, such that augmented tissue function must be supplied for a sufficient period of time for healing or regeneration of damaged natural tissue to occur. The present cells can, for example, supply a product normally produced by kidney or liver tissue to a mammal afflicted with kidney or liver failure, optionally for which a regenerating amount of a morphogen such as OP-1 is being administered concurrently to the mammal.

It will therefore be apparent that the present invention features DNA defining an OP-1 responsive transcription activating element or a portion thereof sufficient for the binding of an intracellular expression activator. The present DNA is in operative association which a cloning site suitable for insertion of a gene, such as a reporter encoding a detectable gene product or a therapeutic gene encoding a product having biological activity. When the reporter gene is inserted at the cloning site, the reporter gene is operatively associated with the morphogen-responsive transcription activating element such that the detectable gene product is produced when present in a cell of the present invention and the cell is contacted with an extracellular inducing agent, such as a morphogen. That is, the DNA described herein serves to induce transcription of the inserted gene. Certain currently preferred embodiments of the present DNA comprise an OP-1 responsive transcription activating element that occurs naturally at least in the promoter region of the mammalian type X collagen gene. Thus, in one particularly preferred embodiment, the sequence of the present DNA comprises nucleotides 697–728 of SEQ. ID No.1, as disclosed herein. The DNA of the present invention advantageously can be contained in a suitable receptacle to provide a kit for facilitating practice of any of the above-described methods. Optionally, the present kits further contain a morphogen and/or a morphogen analog identified according to the present invention.

The foregoing and other objects, features and advantages of the present invention will be made more apparent from the following detailed description of preferred embodiments of the invention.

BRIEF DESCRIPTION OF THE DRAWINGS

The foregoing and other objects, features and advantages of the present invention, as well as the invention itself, will be more fully understood from the following description of preferred embodiments, when read together with the accompanying drawings, in which:

FIG. 4 is an autoradiograph of results of an RNA blot analysis demonstrating the effects of OP-1 on osteoblastic phenotypic markers, such as type I collagen, alkaline phosphatase and osteocalcin, over a 72 hour period.

DETAILED DESCRIPTION OF PREFERRED EMBODIMENTS

Figure 1:
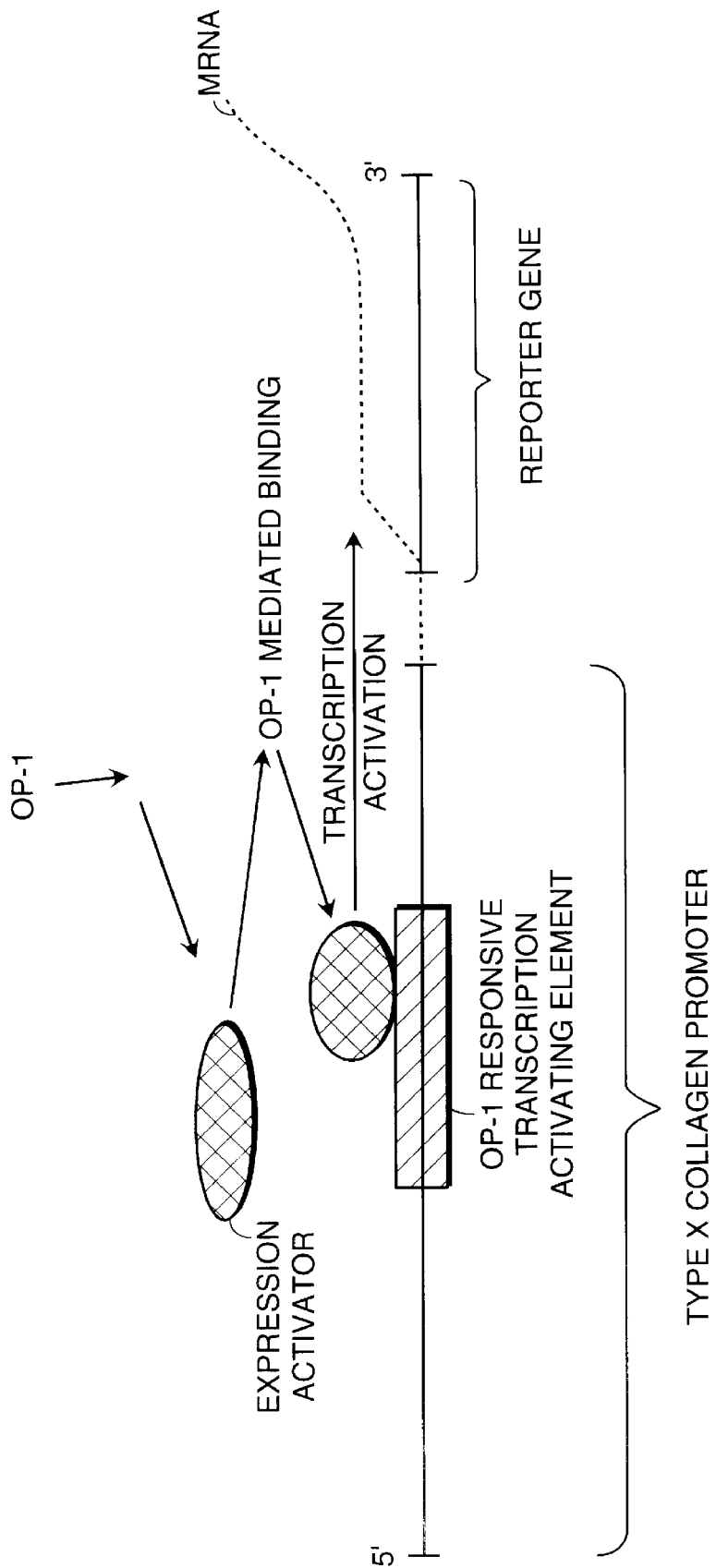
FIG. 1 is a schematic representation of the DNA of the present invention and its usefulness in indicating the presence of an OP-1 mediated biological effect, such as binding of an intracellular substance to the DNA such that transcription of a reporter gene in operative association therewith is induced.

The invention described herein capitalizes on the discovery that morphogens, particularly OP-1, can affect expression of certain genes, present naturally in the genome of mammalian cells. That is, stimulation of mamnmalian cells with OP-1 induces a spectrum of biological effects, including but not limited to the transcriptional activation of selected cellular genes. The promoter region of at least one such gene has been analyzed and, as disclosed herein, found to comprise an OP-1 responsive transcription activating element. The present invention exploits the OP-1 responsive properties of this transcription activating element to advantage in a variety of aspects and embodiments as set forth herein. The present description will be more fully appreciated when viewed in light of the schematic illustration of FIG. 1, which graphically summarizes the anticipated mode of action of the transcription activator of the present invention. FIG. 1 shows the present OP-1 responsive transcription activating element as contained within an OP-1 responsive cell. Following contact of the cell with OP-1, the activating element specifically induces transcription at least of a gene (s) which is situated downstream of and operatively associated with the element. This specific transcriptional activation involves binding of an intracellular substance (an "expression activator") to the OP-1 responsive transcription activating element. This intracellular substance binds with the preferred OP-1 responsive transcription activating element naturally disposed within the promoter region of the mammalian type X collagen gene, at a 5' region of the element which is AT rich and at a 3' region thereof resembling an AP1 binding site sequence. It is shown herein that deletion or mutation of the OP-1 responsive transcription activating element results in loss of OP-1 responsive transcriptional activation of the downstream gene(s) operatively associated with the element.

The present methods and compositions accordingly exploit the OP-1 responsive properties of the newly-discovered transcription activating element. Generally, the methods and compositions of the present invention provide the skilled artisan with the analytical tools and technical know-how sufficient to identify substances (morphogen analogs) that can mimic a biological effect induced by a morphogen such as OP-1. Guidance provided herein accordingly will facilitate evaluation of a variety of diverse substances for morphogen analog properties, thereby broadening the spectrum of potential therapeutic candidates for amelioration and/or treatment of diseases, injuries and deteriorative disorders, such as metabolic bone diseases, for which morphogens are anticipated to provide clinical benefit.

Morphogens, as defined herein, induce or reinduce mammalian cells, particularly uncommitted progenitor cells, to undergo a fully integrated developmental cascade of biological and molecular events that culminate in the morphogenesis of fully differentiated, functional tissue of a type appropriate to the context or local biological environment in which morphogenesis is induced, including any vascularization, connective tissue formation, enervation and the like characteristic of tissue naturally-occurring in such a context. For example, if cells are stimulated by OP-1 in the context of nerve, bone or liver tissue, the resulting cascade of morphogenesis culminates in the formation of new or regenerative differentiated tissue appropriate to the selected local environment Morphogenesis therefore differs significantly from simple reparative healing processes in which scar tissue (e.g., fibrous connective tissue) is formed and fills a lesion or other defect in differentiated, functional tissue.

Further, morphogenesis as contemplated herein occurs in a "permissive environment" by which is meant a local environment that does not stifle or suppress morphogenesis (e.g., regeneration or regenerative healing). Permissive environments exist, e.g., in embryonic tissue or in wounded or diseased tissue, including tissue subjected to surgical intervention. Often, a permissive environment comprises a suitable matrix or substratum to which cells undergoing differentiation can anchor. Exemplary matrices comprise tissue-specific structural components, e.g., collagen or glycosaminogly cans of the same types as occur naturally in the desired tissue. Other components of a permissive environment typically include signals, e.g., cell surface markers or extracellular secreted substances, that direct the tissue specificity of differentiation.

Morphogens are structurally and functionally related to OP-1 and thus include the family of dimeric proteins naturally produced by eukaryotic cells and having tissue-specific morphogenic activity, e.g., activity in inducing endochondral bone morphogenesis, when implanted in a mammal. Morphogens accordingly comprise a subclass of the "super family" of "TGFβ-like" proteins. A morphogen as isolated from natural sources in mature, biologically active form is a glycosylated dimer typically having an apparent molecular weight of about 30–36 kDa as determined by SDS-PAGE. When reduced, the 30 kDa protein gives rise to two glycosylated peptide subunits having apparent molecular weights of about 16 kDa and 18 kDa. The reduced polypeptides themselves have no detectable morphogenic activity. Glycosylation, however, is not required for biological activity. The unglycosylated protein has an apparent molecular weight of about 27 kDa. When reduced, the 27 kDa protein gives rise to two unglycosylated polypeptides having molecular weights of about 14 kDa to 16 kDa. The polypeptides which together form the biologically active dimer comprise at least six, preferably at least seven, positionally conserved cysteine residues as set forth in U.S. Ser. No. 08/396,930, the teachings of which have been incorporated herein by reference.

As stated above, the representative morphogen, for purposes of the present invention, comprises an OP-1 or an OP-1-related polypeptide. Sequences of useful OP-1 polypeptides are recited in U.S. Pat. Nos. 5,011,691; 5,018,753 and 5,266,683; in Ozkaynak et al. (1990) *EMBO J* 9:2085–2093; and Sampath et al. (1993) *Proc. Natl. Acad. Sci. USA* 90: 6004–6008. Additional useful sequences occur in the C-terminal domains of DPP (from Drosophila), Vgl (from Xenopus), 60A (from Drosophila, see Wharton et al. (1991), *Proc. Natl. Acad. Sci. USA* 88:9214–9218), Vgr-1 (from mouse), the OP-1 and OP2 proteins, (see U.S. Pat. No. 5,011,691 by Oppermann et al.), as well as the proteins referred to as BMP2, BMP3, BMP4 (see W088/00205, U.S. Pat. No. 5,013,649 and W091/18098), BMP5 and BMP6 (see WO90111366, PCT/US90/01630) and BMP8 and 9. Each of the foregoing polypeptides, when oxidized and dimerized, is useful as a morphogen herein. Further, this family of morphogenic proteins includes longer forms of a given protein, as well as phylogenetic, e.g., species and allelic variants and biosynthetic mutants thereof, including addition and deletion mutants and variants, such as those which may alter the conserved C-terminal cysteine skeleton, provided that the alteration still allows the protein to form a dimeric species having a conformation capable of inducing morphogenesis, e.g., endochondral bone formation when implanted in a mammal in conjunction with a matrix permissive of bone morphogenesis. In addition, morphogens useful in this invention may include forms having varying glycosylation patterns and varying N-termini, may be naturally occurring or biosynthetically derived, and may be produced by expression of recombinant DNA in procaryotic or eucaryotic host cells according to established techniques. The proteins are active either as homodimers or heterodimers.

Morphogens generally induce all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells. The term "progenitor cells" includes uncommitted cells, preferably of mammalian origin, that are competent to differentiate into one or more specific types of differentiated cells, depending on their genomic repertoire and the tissue specificity of the permissive environment in which morphogenesis is induced. Preferably, morphogenesis culminates in the formation of differentiated tissue having structural and function properties of a tissue that occurs naturally in the body of a mammal.

Morphogens further can delay or mitigate the onset of senescence- or quiescence-associated loss of phenotype and/or tissue function. Morphogens still further can stimulate phenotypic expression of differentiated cells, including expression of metabolic and/or functional, e.g., secretory, properties thereof. In addition, morphogens can induce redifferentiation of transformed cells under appropriate environmental conditions. As noted above, morphogens that induce proliferation and differentiation at least of mammalian bone progenitor cells, and/or support the formation, growth, maintenance and functional properties of mammalian endochondral bone tissue, are of particular interest herein.

Accordingly, a morphogen analog is a substance that mimics a biological effect induced and/or mediated by a morphogen, such as OP-1. Any substance having such mimetic properties, regardless of the chemical or biochemical nature thereof, can be used as a morphogen analog herein. The present morphogen analog can be a simple or complex substance produced by a living system or through chemical or biochemical synthetic techniques. It can be a substance that occurs in nature or a novel substance, e.g., prepared according to principles of rational drug design. It can be a substance that structurally resembles a solvent-exposed morphogen surface epitope implicated in receptor interactions, a substance that otherwise stimulates a morphogen receptor displayed on the surface of a morphogen responsive cell, or a cell-membrane permeant substance that interacts with an intracellular component of the signal transduction machinery of a morphogen responsive cell.

Thus, for example and without being limited hereto, one type of morphogen analog of the present invention can be prepared through judicious application of the principles of biosynthetic antibody binding site (BABS) technology as set forth in U.S. Pat. Nos. 5,132,405, 5,091,513 and 5,258,498, the teachings of which are incorporated herein by reference. BABS analog constructs can be prepared from antibodies, preferably produced by hybridoma cells, that bind specifically to a morphogen cell surface receptor. Alternatively, BABS analysis can be prepared from anti-idiotypic antibodies specifically reactive with the antigen binding site of an antibody that blocks morphogen biological activity. Vulicevic et al. (1994) Biochem. Biophys. Res. Comm. 198:693–700 teaches the preparation of OP-1 specific monoclonal antibodies. Skilled artisans will appreciate that such antibodies can be used as immunogens in the routine preparation of anti-idiotypic antibodies from which BABS analogs of the present invention can be prepared.

A structurally distinct class of morphogen analogs, again set forth herein for illustration and not for limitation, can be prepared through judicious application of the principles of directed molecular evolution as set forth in Tuerk et al. (1990) Science 249:505–510, Famulok et al. (1992) Angew. Chem. Intl. Ed. Engl. 31:979–988 and Bock et al. (1992) Nature 355:564–556, the teachings of each of which are incorporated by reference herein. The directed molecular evolution process involves isolation of a nucleic acid molecule, typically an RNA, that binds with high affinity to a selected ligand such as a protein. Such a nucleic acid molecule is referred to in the art as an "aptamer." The desired aptamer is initially present in a random pool of nucleic acid molecules, and is isolated by performing several rounds of ligand-affinity based chromatography alternating with PCR-based amplification of ligand-binding nucleic acids. Bock et al. (1992), above, have demonstrated the preparations of aptamers, suitable for in vivo use in mammals, that specifically inhibit the blood clot promoting factor, thrombin.

Yet another structurally distinct class of morphogen analogs can be prepared by selecting appropriate members of a random peptide library (Scott et al. (1990) Science 249:386–390) or a combinatorially synthesized random library of organic or inorganic compounds (Needels et al. (1993) Proc. Natl. Acad. Sci. USA 90:10700–10704; Ohlmeyer et al. (1993) Proc. Natl. Acad. Sci. USA 90:10922–10926). Skilled artisans will appreciate that the foregoing and other related technologies, taken together with long-established principles of screening biologically-produced substances, offer a wide array of candidate substances for screening for morphogen analog activity.

Thus, a naturally-sourced OP-1 or morphogen analog can comprise a polypeptide, polynucleotide, carbohydrate, lipid, amino acid, nucleic acid, sugar, fatty acid, steroid, or a derivative of any one of the aforementioned compounds. It can be an intermediate or end product of metabolism of a eukaryotic or prokaryotic cell. Alternatively, the analog can be a biological response modifier or a toxin.

Thus, a morphogen analog identified according to the method of the present invention is a substance that mimics a morphogen by inducing at least one "morphogen-mediated biological effecf" in a morphogen-responsive cell or tissue. The effect can be any biological effect resulting from exposure to or contact with a morphogen, including but not limited to the induction of tissue-specific morphogenesis. Morphogen-mediated biological effects include cellular and molecular responses to morphogen exposure, e.g., as described in 08/115,914, 08/155,343, 08/260,675, 08/165, 541 and 08/174,605, the disclosures of which have been incorporated herein by reference. It will accordingly be appreciated that an "OP-1 mediated biological effect" is any biological effect resulting from exposure to or contact of morphogen-responsive cells or tissue with OP-1, whether in vitro or in vivo. An OP-1 mediated biological effect of particular interest herein includes stimulation of the expression of one or more specific gene(s), including stimulation of the binding of an intracellular substance to DNA expression regulation elements. Other OP-1 mediated biological effects include stimulation of cellular proliferation, cellular differentiation, maintenance of a differentiated phenotype, and, under the appropriate circumstances, induction of redifferentiation. Further preferred OP-1 mediated biological effects are molecular or biochemical effects associated with tissue-specific morphogenesis, e.g., endochondral bone formation or nerve regeneration.

Specific OP-1 mediated biological effects associated with endochondral bone formation include induction of mitogenesis and phenotypic markers for chondrocyte and osteoblast differentiation in fetal rat calvaria cells. Useful induced phenotypic markers include types I, II and X collagen; alkaline phosphatase; and osteocalcin. Thus, a candidate compound identified as an OP-1 analog using the methods and compositions of the instant invention can mimic OP-1 by inducing at least one of the foregoing biological effects.

Accordingly, in a first aspect, the present invention features a method of identifying a morphogen analog that induces an OP-1 mediated biological effect. This method involves the step of providing a test cell comprising DNA defining an OP-1 responsive transcription activating element, and, in operative association therewith, a reporter gene encoding a detectable gene product. The present OP-1 (or morphogen) responsive transcription activating element is a cis-acting DNA element, a preferred sequence of which is disclosed herein, that modulates expression of a downstream gene in an OP-1 (or morphogen) responsive cell. The OP-1 responsive transcription activating element can be located between about 100–600 base pairs, preferably about 250–400 base pairs, upstream of the gene's transcriptional initiation site. Regardless of its exact relative location, the OP-1 responsive element is in operative association with the downstream gene if its activation stimulates transcription thereof. That is, when OP-1 binds to the cell surface of an OP-1 responsive cell and thereby induces an intracellular cascade of biological responses, one such response comprises induction of expression of this downstream gene. Evidence presented herein indicates that this effect is accomplished via the binding of an intracellular substance (referred to as an expression activator) to the OP-1 responsive transcription activating element.

The present test cell is any cell comprising DNA defining an OP-1 responsive transcription activating element operatively associated with a reporter gene encoding a detectable gene product. Such DNA can occur naturally in a test cell or can be a transfected DNA. Thus, the test cell can optionally be an OP-1 responsive cell. An "OP-1 responsive cell" is any cell that displays a receptor on its surface to which OP-1 binds to induce an intracellular OP-1 mediated biological effect. A morphogen responsive cell is herein defined similarly. The induced intracellular biological effect is characteristic of morphogenic biological activity, such as activation of a second messenger cascade of events involving for example, cyclic nucleotides, diacylglycerol, and/or and other indicators of intracellular signal transduction such as activation or suppression of gene expression, including induction of mRNA resulting from gene transcription and/or induction of protein synthesis resulting from translation of MRNA transcripts indicative of tissue morphogenesis. Exemplary OP-1 responsive cells are preferably of mammalian origin and include, but are not limited to, osteogenic progenitor cells; calvaria-derived cells; osteoblasts; osteoclasts; osteosarcoma cells and cells of hepatic or neural origin. Any such OP-1 or morphogen responsive cell can be a suitable test cell for assessing whether a candidate substance induced is a morphogen analog.

The present identification method is carried out by exposing a test cell to at least one candidate substance and, detecting whether such exposure induces expression of the detectable gene product that is in operative association with the OP-1 responsive transcription activating element of the present invention. Expression of this gene product indicates that the candidate substance can induce an OP-1 mediated biological effect. Skilled artisans can, in light of guidance provided herein, construct a test cell with a responsive element from an OP-1 responsive cell and a reporter gene of choice, using recombinant vectors and transfection techniques well-known in the art. There are numerous well-known reporter genes useful herein. These include, for example, chloramphenicol acetyltransferase (CAT), luciferase, human growth hormone (hGH), beta-galactosidase, assay systems and reagents which are available through commercial sources. As will be appreciated by skilled artisans, the listed reporter genes represent only a few of the possible reporter genes that can be used herein. Examples of such reporter genes can be found in F. A. Ausubel et al., Eds., *Current Protocols in Molecular Biology*, John Wiley & Sons, New York, (1989). Broadly, any gene that encodes a detectable product, e.g., any product having detectable enzymatic activity or against which a specific antibody can be raised, can be used as a reporter gene in the present identification method.

A currently preferred reporter gene system is the firefly luciferase reporter system. (Gould, S. J., and Subramani, S. (1988) *Anal. Biochem.*, 7:404–408 incorporated herein by reference). The luciferase assay is fast and sensitive. In this assay system, a lysate of the test cell is prepared and combined with ATP and the substrate luciferin. The encoded enzyme luciferase catalyzes a rapid, ATP dependent oxidation of the substrate to generate a light-emitting product. The total light output is measured and is proportional to the amount of luciferase present over a wide range of enzyme concentrations.

CAT is another frequently used reporter gene system; a major advantage of this system is that it has been an extensively validated and is widely accepted as a measure of promoter activity. (Gorman C. M., Moffat, L. F., and Howard, B. H. (1982) *Mol. Cell. Biol.*, 2:1044–1051 incorporated herein by reference). In this system, test cells are transfected with CAT expression vectors and incubated with the candidate substance within 2–3 days of the initial transfection. Thereafter, cell extracts are prepared. The extracts are incubated with acetyl CoA and radioactive chloramphenicol. Following the incubation, acetylated chloramphenicol is separated from nonacetylated form by thin layer chromatography. In this assay, the degree of acetylation reflects the CAT gene activity with the particular promoter.

Another suitable reporter gene system is based on immunologic detection of hGH. This system is also quick and easy to use. (Selden, R., Burke-Howie, K. Rowe, M. E., Goodman, H. M., and Moore, D. D. (1986), Mol. Cell, Biol., 6:3173–3179 incorporated herein by reference). The hGH system is advantageous in that the expressed hGH polypeptide is assayed in the media, rather than in a cell extract. Thus, this system does not require the destruction of the test cells. It will be appreciated that the principle of this reporter gene system is not limited to hGH but rather adapted for use with any polypeptide for which an antibody of acceptable specificity is available or can be prepared.

Regardless of the reporter gene system used, the candidate substance is exposed to the test cell for a sufficient period of time and under sufficient cell culture conditions for the OP-1 mediated biological effect (production of the detectable gene product) to be induced. For example, using the presently preferred OP-1 responsive transcription activating element and fetal rat calvaria cells as described in the Examples below, the OP-1 mediated biological effect is induced at least upon about 24 hr of exposure to OP-1. Thus, candidate substances diluted to appropriate, non-toxic, biologically relevant concentrations and exposed to the rat calvaria test cell of the present examples, are anticipated to induce production of the detectable gene product at least upon about 16 hr, preferably about 24 hr and prior to about 36 hr of exposure to said cell thereto. Suitable cell culture conditions for the exposure step will vary depending on the precise nature of the test cell and can be optimized by the skilled artisan through no more than routine experimentation.

Additionally, the skilled artisan can practice certain other embodiments of the instant method once a putative morphogen analog is identified using the above-described identification method. That is, confirmatory screening of the putative analog can involve the additional steps of contacting an OP-1 responsive cell therewith and detecting induction of a biological effect known to be mediated by OP-1 in the OP-1 responsive cell. Induction of the biological effect further confirms the substance's identity as a potential OP-1 (or morphogen) analog. Skilled artisans will appreciate that, under certain circumstances, detecting expression of the reporter gene and detecting induction of the biological effect can occur concurrently. Similarly, the test cell can itself be OP-1 responsive.

Certain other embodiments of the instant method can permit further confirmatory screening of the above-identified putative analog. Such optional methods involve the additional steps of providing the putative analog to a morphogenically permissive, tissue-specific locus in a mammal and detecting induction of tissue-specific morphogenesis at the locus, the induction being indicative of the analog's ability to induce tissue-specific morphogenesis in a mammal. This embodiment allows the skilled artisan to confirm with reasonable certainty that a promising substance indeed has utility as an OP-1 or morphogen analog.

A morphogen analog identified as described above accordingly can be produced in therapeutic-grade commercially-significant quantities and formulated for administration to a mammal, preferably to humans for therapeutic effect. If desired, e.g., to reduce toxicity, improve shelf life or biological potency, a derivative of the identified morphogen analog having substantially the same morphogen-mimetic properties thereof also can be produced.

Any appropriate method can be used for production of a particular morphogen analog. For example, such methods can include, but are not limited to, methods of biological production, such as from a host cell or synthetic production of a peptide. Additionally, methods can include non-biological chemical synthesis. Still other methods can include production by fermentation or cell culture using a cell producing the analog compound. Naturally-sourced analogs can be, for example, expressed from intact or truncated genomic or cDNA, or from synthetic DNAs in procaryotic or eucaryotic host cells, and purified, cleaved, refolded and oxidized as necessary to form active molecules. Useful host cells include prokaryotes including E coli and B. subtilis, and eucaroyotic cells including mammalian cells such a fibroblast 3T3 cells, CHO, COS, melanoma or BSC cells, Hela and other human cells, the insect/baculovirus system, as well as yeast and other microbial host cell systems. Alternatively, proteins can be chemically synthesized using standard chemical peptide synthesis methodologies well described in the art and commercially available. Similarly, non-peptide molecules can be chemically synthesized using standard chemical protocols.

In another aspect, the present invention features DNA for inducing an OP-1 mediated biological effect. The present DNA defines an OP-1 responsive transcription activating element such that the DNA, when present in an OP-1 responsive cell contacted with OP-1, serves to induce transcription of a gene located downstream of an in operative association with the aforesaid element. Specifically, in one embodiment, the sequence of DNA defining the OP-1 responsive transcription activating element is most preferably that depicted by core nucleotides 697–728 of SEQ. ID No. 1 described herein. In another embodiment, the preferred DNA is depicted by nucleotides 682–731 of SEQ. ID No. 1 which includes nucleotides 682–696 flanking the core sequence at the 5' end and nucleotides 729–731 flanking the core sequence at the 3' end. In yet another embodiment, the preferred DNA is depicted by nucleotides 682–761 of SEQ. ID No. 1 which further includes nucleotides 682–696 flanking the core sequence at the 5' end and nucleotides 729–761 flanking the core sequence at the 3' end. Additionally, the instant invention embraces DNA which hybridizes specifically with any one of the above-described DNA sequences. As used herein, "hybridizes specifically" means hybridizes under conditions that are defined in the art as low stringency conditions. An exemplary set of conditions is thus: hybridization in 30% formamide, 1M NaCl, 50 mM Tris (pH 7.5), 0.5% SDS, 10% Dextran Sulfate, 1X Denhardt's Solution, and 1 mg/ml denatured salmon sperm DNA for a total of 20 hours at 42° C., followed by washing at room temperature once in 2X SSC/0.1% SDS, and then twice at 55° C. in 1X SSC/0.1% SDS for fifteen minutes each. See, e.g., U.S. Pat. No. 5,359,047 the disclosure of which is herein incorporated by reference.

Thus, the currently preferred OP-1 responsive transcription activating element comprises the nucleotides at positions 697–728 of SEQ. ID No. 1. This particular core sequence is expected to hybridize specifically with a DNA binding site sequence resembling an AP1 DNA sequence previously described in the art (SEQ. ID No. 2; see, e.g., Lee et al. (1989) Cell 49: 741–752). As depicted by nucleotides at positions 697–712 of SEQ. ID No. 1, the 5' end of this core sequence is AT rich while the 3' end (nucleotides 715–724 of SEQ. ID No. 1) contains a sequence resembling an AP1 binding site.

As disclosed herein, a mutation within the nucleotide sequence of the instant OP-1 responsive transcription activating element results in a loss of OP-1 responsiveness (SEQ. ID No. 3). Specifically, mutation of the 3' sequence resembling the AP1 binding site abolishes OP-1 responsiveness. That is, mutation abrogates the ability of the intracellular activator mentioned above to bind to the present transcriptional activating element.

Thus, in another aspect, the present invention provides a substantially pure substance competent to bind to the above-mentioned OP-1 responsive transcription activating element, or a portion thereof, such that the substance has the property of modulating expression of a gene encoding a gene product when the above-described DNA is in operative association therewith and the substance is bound thereto. In a currently preferred embodiment, this substantially pure substance, referred to herein as an expression activator, binds to the core sequence of the currently preferred OP-1 responsive element, e.g., to nucleotides 697–728 of SEQ. ID No.1, thereby modulating expression of a downstream gene encoding a gene product operatively associated with the responsive element As discussed earlier and exemplified herein below, a currently preferred substance is a proteinaceous intracellular substance having general immunological properties of a fos family protein. That is, in one currently preferred embodiment, the substance comprises a polypeptide having an amino acid sequence which shares immunoreactivity with the conserved domain of human c-fos; specifically, with amino acid residues 128–152 of human c-fos protein as depicted by amino acid residues 1–25 in SEQ. ID No. 4. In particular, one exemplary substance comprises an epitope which is bound by the antibody designated "c-fos (K-25)" available as Catalog No. sc-253 from Santa Cruz Biotechnology, Inc., Santa Cruz, Calif. This antibody is a rabbit affinity-purified polyclonal antibody raised against a peptide corresponding to amino acids 128–152 mapping within a highly conserved domain of human c-fos p62. Human c-fos p62 is a 64 kd nuclear phosphoprotein induced by a variety of biologically active agents and is a component of the transcriptional regulator, AP1. (See, e.g., Bohmann et al. (1987), *Science* 238:1386–1392). The antibody c-fos (K-25) reacts with vertebrate c-fos and the well-known functional homologs of c-fos known as fos B, fra-1 and fra-2 by immunoprecipitation, Western blotting and cell staining. See, e.g., Cohen et al. (1989), *Genes and Dev.* 3:173–184 and Nishina et al. (1990), *Proc. Natl. Acad. Sci. USA* 87:3619–3623.

Also contemplated herein are amino acid variants of the present intracellular expression activator including allelic and species variants thereof or other naturally-occurring or synthetic amino acid sequence variants. As used herein, an "amino acid sequence variant" comprises a polypeptide having an amino acid sequence which differs from the naturally-occurring sequence, yet which retains substantially the same functional properties as the activator reported in the examples below, including the binding capacity for nucleotides 682–761 of SEQ. ID No. 1.

It is contemplated that the substantially pure expression activator can be prepared using well-known purification techniques such as, but not limited to, gel filtration chromatography, affinity chromatography, and high-pressure liquid chromatography. In particular, it can be prepared by ligand-affinity chromatography based upon its binding the transcription activating element of SEQ. ID No. 1 herein. The skilled artisan need only use routine experimentation to obtain a substantially pure activator in accordance with the instant invention.

In a related aspect, the instant invention further provides a method for assessing whether a sample comprises such an activator. This method involves providing the above-described core DNA sequence; contacting the DNA with the sample; and, detecting binding thereto by the activator. If desired, an equivalent of the core DNA sequence can be used, including allelic, species and degenerate sequences. "Degenerate sequences" include nucleotide sequences which differ from the present core sequence but which do not alter the binding interaction between the above-described intracellular expression activator and the intact OP-1 responsive transcription activating element. This method provides both an alternative to, or an additional screening assay for, an OP-1 or morphogen analog because, as exemplified below, a morphogen such as OP-1 induces and/or mediates the binding of this substance to the responsive element. Thus, screening for an OP-1 induced interaction, for example, between the DNA and such a substance further characterizes a compound's ability to mimic OP-1, for example. Exemplary conditions under which such a DNA-protein interaction can be detected have been previously described in Augereau et al. (1986), *EMBO J.* 5:1791–1797, the disclosure of which is herein incorporated by reference. Briefly, protein-containing nuclear extracts are pre-incubated on ice for 15 minutes with *E. coli* DNA in 10% glycerol, 10 mM Hepes, pH 7.9, 50 mM KCl, 5 mM $MgCl_2$, 0.5 mM DTT; upon addition of the particular DNA sequence of interest, incubation is allowed to continue for 15 minutes to permit protein-DNA complex formation.

In yet another aspect, the invention provides a cell for the inducible expression of a morphogen. This cell has a first DNA encoding a morphogen; a second DNA in transcriptionally operative association with the first DNA, the second DNA comprising the above-described OP-1 responsive transcription activating element, e.g., comprising nucleotides 682–761 of SEQ. ID No.1, or a functional equivalent thereof. The cell further comprises cellular means for producing an intracellular substance (an expression activator) that binds with the second DNA so as to stimulate expression of the morphogen encoded by the first DNA when the cell is contacted with an extracellular inducing agent. In certain preferred embodiments, the extracellular inducing agent is a morphogen or an analog thereof identified according to the inventive principles set forth herein. In certain embodiments, the extracellular inducing agent is OP-1 or an analog thereof.

The foregoing cell is a mammalian cell, preferably a primate cell, most preferably a human cell. In certain embodiments, the foregoing cell is a murine cell such as a mouse, rat or hamster cell. The cell of the instant invention can be naturally-occurring, immortalized in culture or constructed by recombinant or cell fusion technologies.

It will be appreciated that the present invention can be used to construct a cell for the inducible expression of any desired gene product and is not limited to use with first DNA encoding a morphogen. In still another aspect, the invention provides methods for inducing expression, including autocrine expression, of a morphogen, e.g., OP-1, indeed of a gene product using the above-described cells. In these methods, one of the above-described cells is contacted with OP-1, a morphogen or a morphogen analog under conditions sufficient to induce expression of the gene product encoded by the first DNA.

Optionally, the foregoing methods can be carried out in vivo by providing any one of the above-described cells to a mammal. In these embodiments, the contacting step is carried out by administering an inducing agent to the mammal. This method is particularly well suited for administering a morphogen such as, but not limited to, OP-1 to a mammal afflicted with a metabolic bone disease or other injury, disease or condition for which long-term administration of the morphogen is anticipated to provide a clinical benefit.

In yet another currently preferred embodiment, the invention provides DNA for inducing a morphogen mediated biological effect This DNA defines a morphogen-responsive transcription activating element and a cloning site suitable for insertion of a reporter gene encoding a detectable gene product, or a therapeutic gene encoding a biologically active gene product. When the reporter gene is inserted at the cloning site, the reporter gene is operatively associated with the morphogen-responsive transcription activating element such that the detectable gene product is produced when the DNA is present in a morphogen-responsive cell and the cell is contacted with a morphogen or an analog thereof. In certain currently preferred embodiments, the morphogen-responsive transcription activating element is responsive to OP-1 or an analog thereof. The materials and protocols for inserting reporter genes within pre-existing cloning sites are readily available and well-known in the art. See, for example, *Molecular Cloning: A Laboratory Manual* (eds., Maniatis et al.; Cold Spring Harbor Press, Cold Spring Harbor; 2nd edition)(1989). The skilled artisan need only exercise routine experimentation to prepare DNAs of the present invention.

Accordingly, for ease of practice of the invention set forth herein, a kit is provided for screening candidate substances for morphogen mimetic properties as is a kit for preparing a cell for the inducible production of a gene product. The kits herein comprise a receptacle for containing DNA, and DNA defining an OP-1 responsive transcription activating element and a cloning site suitable for insertion of a gene in operative association with the activating element. Optionally, the DNA comprises a reporter gene encoding a detectable gene product, e.g., a product having detectable enzymatic activity. In certain embodiments, kits further contain means for inducing a cell to internalize the present DNA. Certain other kits contain a morphogen and/or a compound identified by the methods of the instant invention as having the ability to induce a morphogen-mediated or OP-1 mediated biological effect. These optional kit components are useful as control substances for practice of the identification methods disclosed herein.

Practice of the invention will be still more fully understood from the following examples, which are presented herein for illustration only and should not be construed as limiting the invention in any way.

EXAMPLE 1

Effect of OP-1 on the Proliferation and Differentiation of C5.18 Cells

To characterize the biological effects of OP-1 on bone derived cell lines, OP-1 responsiveness was examined in C5.18 cells, spontaneously immortalized fetal rat calvaria cells well-known in the art and described, for example, in Grigoriadis et al. (1990) *Developmental Biology* 142:313–318 and in Von Schroeder et al. (1994) *Teratology* 50:54–62, the disclosures of which are herein incorporated by reference. C5.18 cells were plated in 12-well culture dishes ($1 \times 10^5$ cell/well) in αMEM containing 15% fetal bovine serum. As described below, varying amounts of recombinant human OP-1 (Creative BioMolecules, Inc., Hopkinton, Mass.) were added to the culture media and the calvaria cells were incubated with the OP-1 containing medium for varying lengths of time as indicated below. OP-1 was prepared and formulated generally as earlier described in U.S. Pat. Nos. 5,258,494; 5,266,683; and 5,354,557, the disclosures of which are incorporated herein by reference.

Briefly, OP-1 treatment of fetal rat calvaria cells induced mitogenesis and phenotypic markers for chondrocytes and osteoblasts. For example, OP-1 induced type II collagen, a marker for chondrocytes, and type X collagen, a specific marker for hypertrophic chondrocytes, respectively. Subsequently, OP-1 induced type I collagen and the osteoblastic markers, osteocalcin and alkaline phosphatase. The orderly appearance of these molecular markers recapitulated the sequence of events observed during endochondral bone morphogenesis as induced in vivo by OP-1. See U.S. Pat. No. 4,968,590 and Sampath et al. (1983) Proc. Natl. Acad. Sci. USA 80:6591–6595, the disclosures of which are incorporated herein by reference.

The osteoblastic markers alkaline phosphatase and osteocalcin, as well as the chondrocytic markers types II and X collagen, were examined using standard techniques for RNA blot analysis such as those disclosed in Harada et al. (1994) J. Clinical Investigation 93:2490–2496. cDNA probes for rat alkaline phosphatase and osteocalcin were prepared in accordance with art-recognized methods such as, for example, those disclosed in Yoon et al. (1987) Biochem. Biophys. Res. Commun. 148:1129–1136. cDNA probes for mouse types II and X pro-collagen were also prepared in accordance with art-recognized methods such as those disclosed in Asahina et al. (1993) J. Cell Biology 123:921–933 and Chen et al. (1995) J. Cell Science 108:105–114, respectively. Relevant teachings of each of the aforementioned references are incorporated herein by reference.

Figure 2:
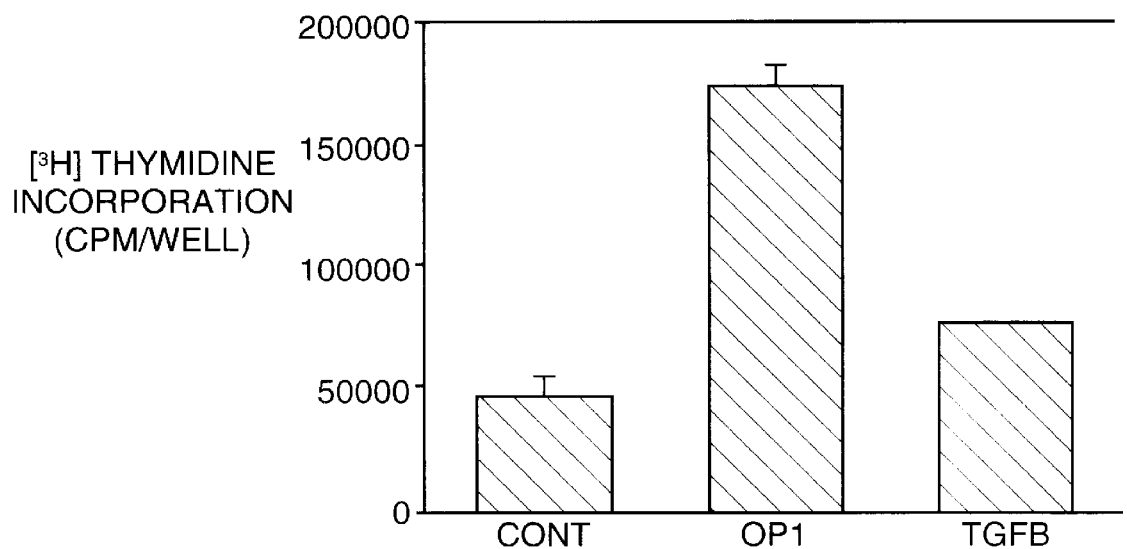
FIG. 2 is a bar graph illustrating the effects of OP-1 and TGFβ on proliferation of C5.18 fetal calvaria cells using $^3$H-thymidine incorporation as a measure of mitogenesis.

Specifically, 300 ng/ml OP-1 induced mitogenesis (FIG. 2) as measured by $^3$H-thymidine incorporation studies practiced generally according to art-recognized methods. FIG. 2 illustrates that OP-1 (300 ng/ml) stimulated $^3$H-thymidine uptake. This same result was not obtained in control cultures without OP-I or cultures treated only with TGFβ (porcine; Catalog #102-B2, R and D Systems, Inc., Minneapolis, Minn.).

Figure 3:
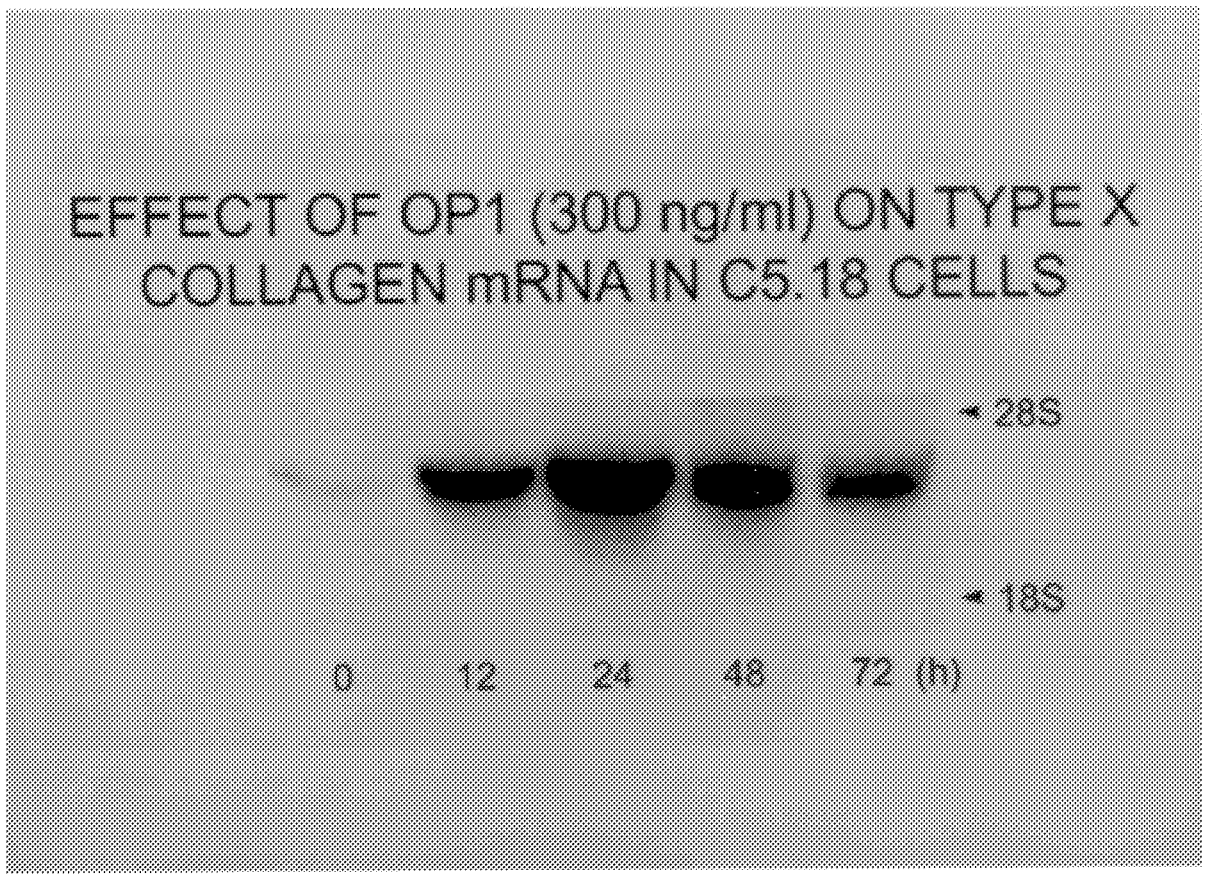
FIG. 3 is an autoradiograph of results of an RNA blot analysis demonstrating the effects of OP-1 on type X collagen mRNA in C5.18 fetal calvaria cells over a 72 hour period.

The effects of OP-1 on expression of phenotypic markers for chondrocytes and osteoblasts were also studied. As illustrated, OP-1 induced type II collagen, a marker for matrix-producing chondrocytes, and type X collagen, a specific marker for hypertrophic chondrocytes, at 12 h and 24 h, respectively (FIG. 3). Furthermore, OP-1 induced type I collagen at 48 h and, at 72 h, induced expression of osteocalcin and alkaline phosphatase, both of which are well-characterized as osteoblastic markers (FIG. 4).

Figure 5:
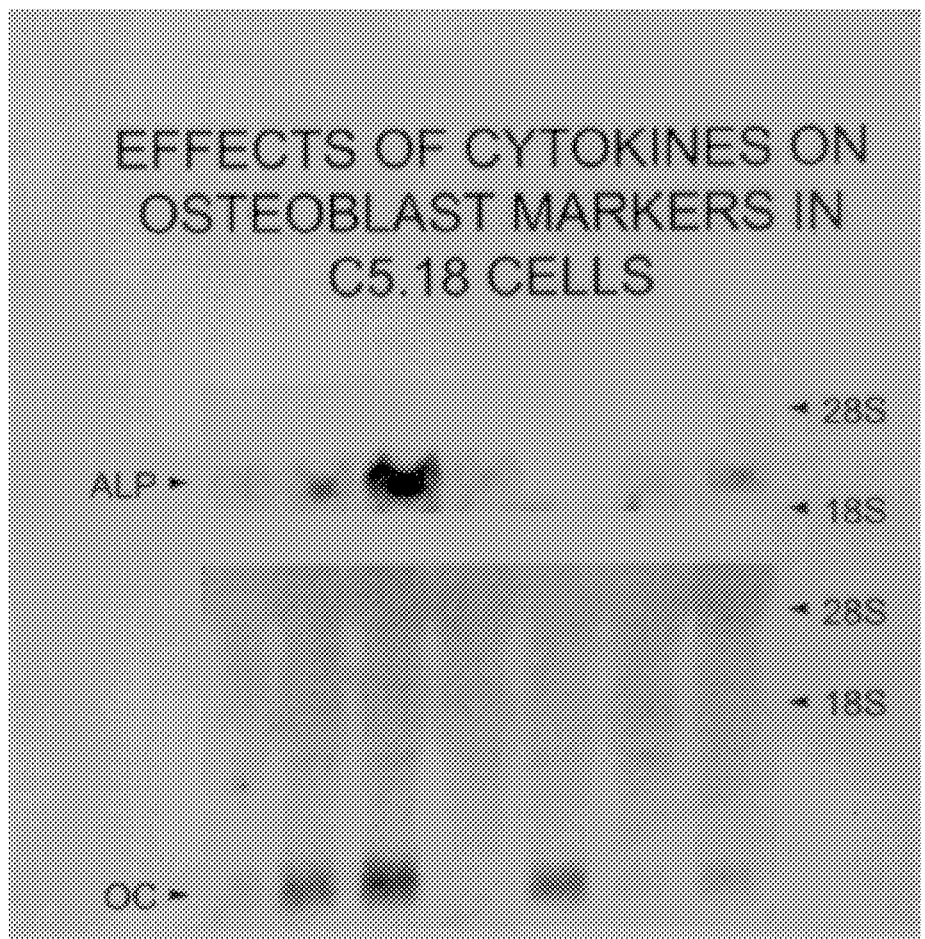
FIG. 5 is an autoradiograph of results of an RNA blot analysis demonstrating the effects of OP-1 and TGFβ on osteoblastic phenotypic markers, such as alkaline phosphatase and osteocalcin.
Figure 6:
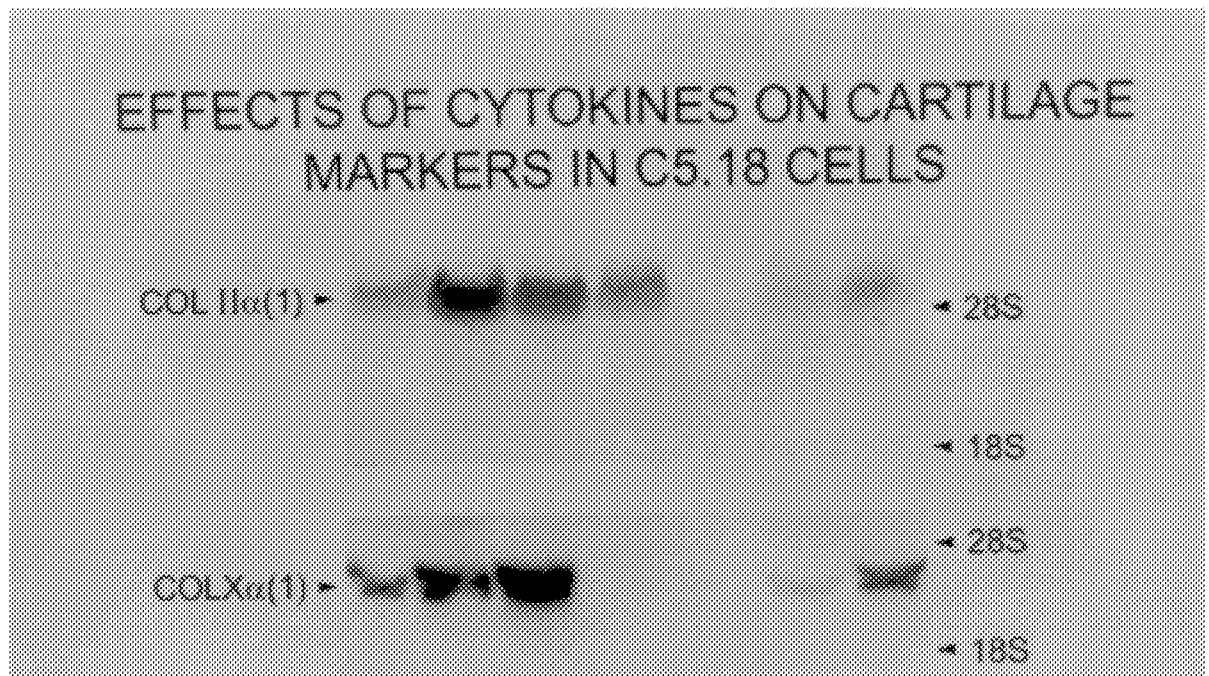
FIG. 6 is an autoradiograph of results of an RNA blot analysis demonstrating the effects of OP-1 and TGFβ on chondrocytic phenotype markers, such as types II and X collagen.

Thus, in fetal rat calvaria cells, OP-1 induced a cascade of molecular events resembling the sequence of events induced in vivo by OP-1 and culminating in endochondral bone formation. OP-1 also induced formation of nodules positive for alkaline phosphatase. In contrast, TGFβ elicited negligible effect on the expression of these same osteoblastic (FIG. 5) or chondrocytic markers (FIG. 6). These observations suggest that C5.18 cells provide a useful cell culture model for assessing whether test substances function as OP-1 analogs, as well as for further delineating one or more of the biological mechanisms associated with OP-1 induced chondrocyte and/or osteoblast differentiation.

Those of skill in the art will appreciate that the general principles and parameters of the C5.18-based in vitro model system, including monitoring expression of phenotypic markers such as types I, II and X collagen, and alkaline phosphatase, can be adapted easily to other readily available cell culture systems. See, e.g., Manduca et al. (1992) Cell Biology 57: 193–201 for a description of a chick embryo osteoblast in vitro assay system; Reginato et al. (1993) Dev. Dyn. 198: 284–295 for a description of a chick embryonic sternum system; Asahina et al. (1993) J. Cell Biology 123: 921–933 for a description of an in vitro system using primary cultures of newborn rat calvaria. The disclosures of the aforementioned prior art references are incorporated herein by reference.

EXAMPLE 2

Effects of OP-1 on Type X Collagen Promoter

The above-described effect of OP-1 on the expression of type X collagen was of particular interest as this phenotypic marker is generally understood to be specific for hypertrophic chondrocytes and thus of endochondral bone formation. A more in depth study of the responsiveness of the type X collagen gene to OP-1 was carried out as follows:

The promoter region of the mouse type X collagen gene (nucleotides 1 to 1067, as designated by Elima et al. (1993) Biochem. J. 289:247–253, and by GenBank EMBL Data Bank: Accession #X67348; COLI0AL gene; collagen alpha 1 type X)(also designated herein as nucleotides 1–1067 of SEQ. ID No. 1) was cloned according to well-known PCR (polymerase chain reaction) methods from mouse genomic DNA (Clonetech, Palo Alto, Calif.) using a 34 base pair 5' primer carrying the KpnI site and a 33 base pair 3' primer carrying the MluI site. These primer sequences were confirmed using the sequence of the mouse type X collagen promoter as published in Elima et al. (1993) Biochem. J. 289:247–253, the disclosure of which is incorporated herein by reference. The sequence of cloned type X collagen promoter DNA used herein was confirmed by nucleotide sequencing, using the Sequence Version 2.0 DNA Sequencing Kit available from USB (United States Biochemical, Cleveland, Ohio).

Figure 7:
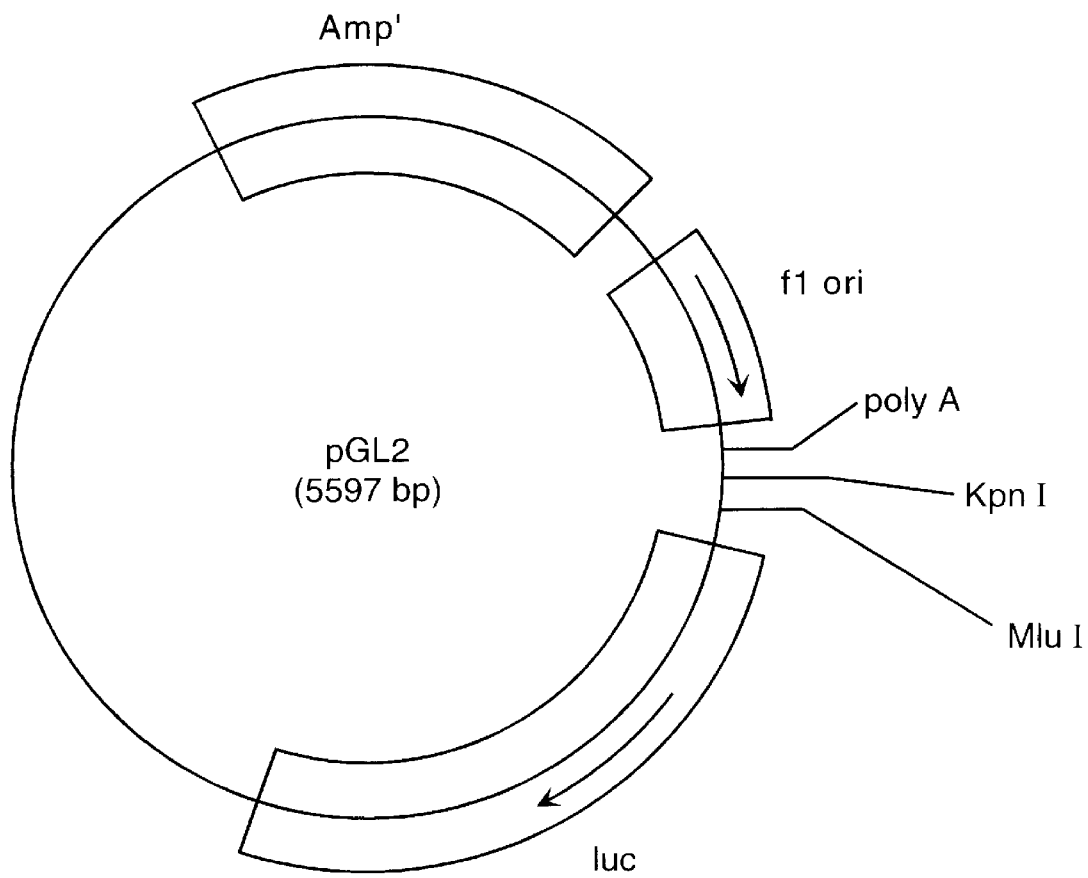
FIG. 7 is a vector map depicting an exemplary vector with a promoterless luciferase reporter gene and the KpnI and MluI restriction enzyme cloning sites.

The cloned promoter DNA was used to prepare a series of deletion construct vectors carrying the luciferase reporter gene and portions of the mouse type X collagen gene. A promoterless pGL2-basic plasmid comprising a nucleotide sequence encoding the detectable enzyme luciferase (Promega, Madison Wisc.) was employed as the basic vector (FIG. 7). The above-described intact mouse type X collagen promoter sequence (SEQ. ID No. 1) was inserted into the pGL2 plasmid following digestion with KpnI and MluI. Similarly, serial 5' deletion fragments (prepared by PCR methods as described above) were subcloned into KpnI and MluI digested preparations of the pGL2 plasmid. Thus, the cloned promoter DNA or a portion thereof was placed in transcriptionally operative association with the luciferase reporter gene.

The foregoing vectors were transfected into calvaria cells using standard techniques. C5.18 cells were plated in 12-well culture dishes ($1 \times 10^5$ cell/well) in αMEM containing 15% fetal bovine serum (complete media). Seventy-two hours later, the above-described vectors were transfected into the cultured cells using a calcium phosphate method in complete medium for 6 hours. A 10% solution DMSO in PBS was used to terminate transfection. Thereafter, transfected cells were cultured in complete media. Twenty-four hours later, transfected cells were contacted with OP-1 and further cultured for an additional 24 hours. Luciferase activity induced by the exogenously added OP-1 was measured using the Promega Luciferase Assay System (Promega, Madison Wisc.).

Figure 8:
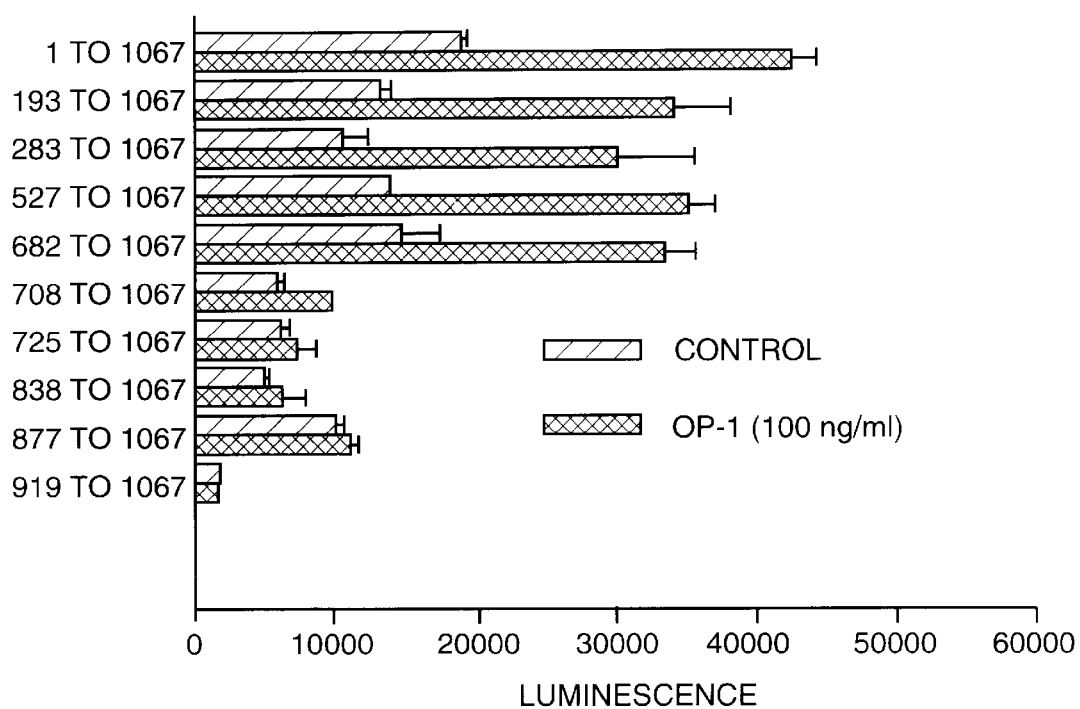
FIG. 8 is a bar graph depicting OP-1 induced luminescense of various deletion constructs of the type X collagen promoter operatively associated with the luciferase reporter gene and transfected into C5.18 fetal calvaria cells subsequently contacted with OP-1.

As illustrated in FIG. 8, OP-1 treatment (100 ng/ml) stimulated the luciferase activity of the intact type X collagen construct containing the 1067 base pair fragment of the COLX promoter (nucleotides 1–1067 of SEQ. ID No. 1). This same amount of OP-1 stimulated the construct containing a 387 base pair fragment (nucleotides 682–1067 of SEQ. ID No. 1) of the COLX promoter up to approximately about 3 fold. However, deletion of a further 42 base pair 5' fragment abolished OP-1 responsiveness. From this result, it was inferred that at least the nucleotides at positions 682–723 of SEQ. ID No. 1 are responsible for OP-1 responsiveness of the type X collagen gene.

Further studies confirmed that the 80 bp nucleic acid fragment comprising residues 682–761 of SEQ. ID No. 1 is sufficient to confer OP-1 responsiveness to the COLX promoter or to a heterologous (RSV) promoter. These studies, results of which are set forth in FIGS. 9 and 10, were carried out using both the above-described COLX promoter vector and a well-known RSV-promoter-driven luciferase vector (see, for example, Towler et al. (1995) *Endocrinology* 136:1089–1096, the disclosure of which is incorporated herein by reference), and the general transfection and luciferase assay procedures set forth above.

Figure 9:
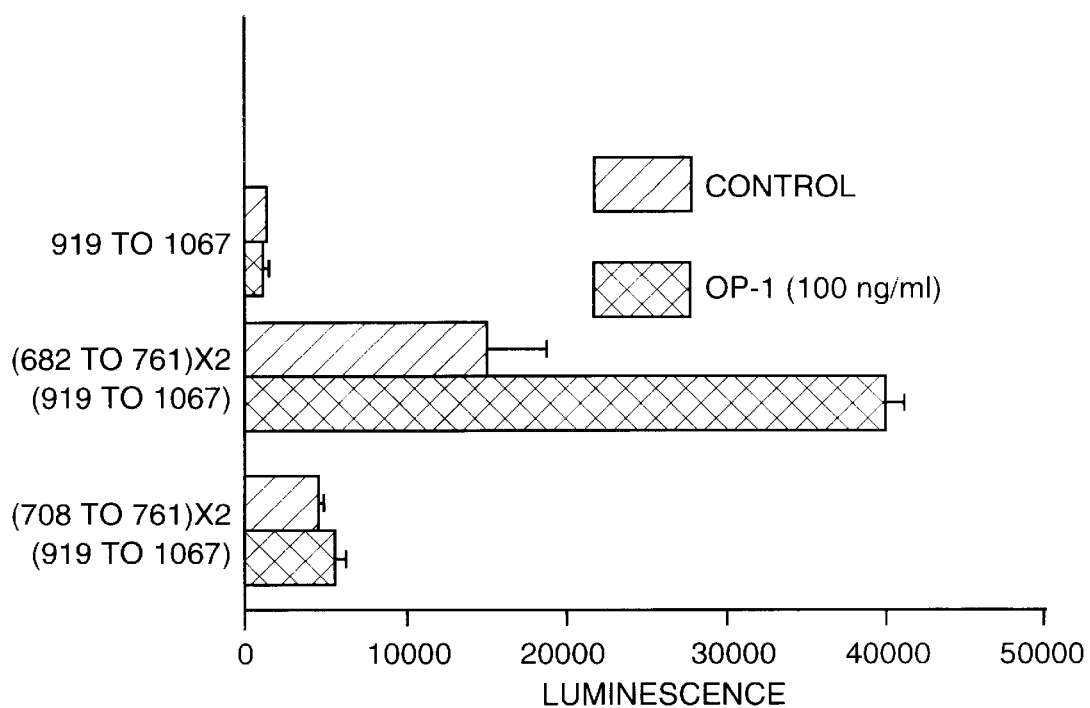
FIG. 9 is a bar graph depicting OP-1 induced luminescence of selected deletion constructs which confer OP-1 responsiveness to a minimum segment of the homologous type X collagen promoter.
Figure 10:
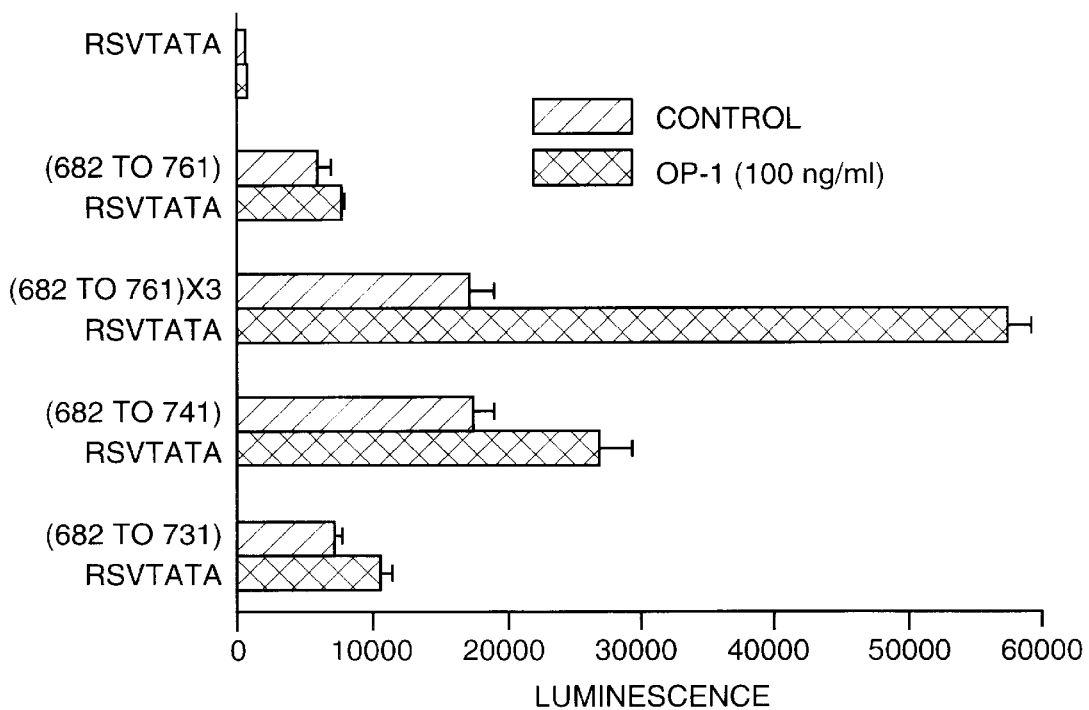
FIG. 10 is a bar graph depicting OP-1 induced luminescence of selected deletion constructs which confer OP-1 responsiveness to a minimum segment of the non-homologous (heterologous) RSV promoter.

Still further studies resting on 3' deletion analysis of the RSV promoter construct more precisely identified the OP-1 responsive element as a 50 base pair sequence spanning positions 682–731 of SEQ. ID No. 1 (FIG. 10). Furthermore, deletion of 26 base pairs represented by nucleotides 682–707 of SEQ. ID No. 1 abolished OP-1 responsiveness, suggesting that a 5' AT rich sequence spanning nucleotides 697–712 of SEQ. ID No. 1 is required for OP-1 responsiveness (FIG. 9).

Figure 11:
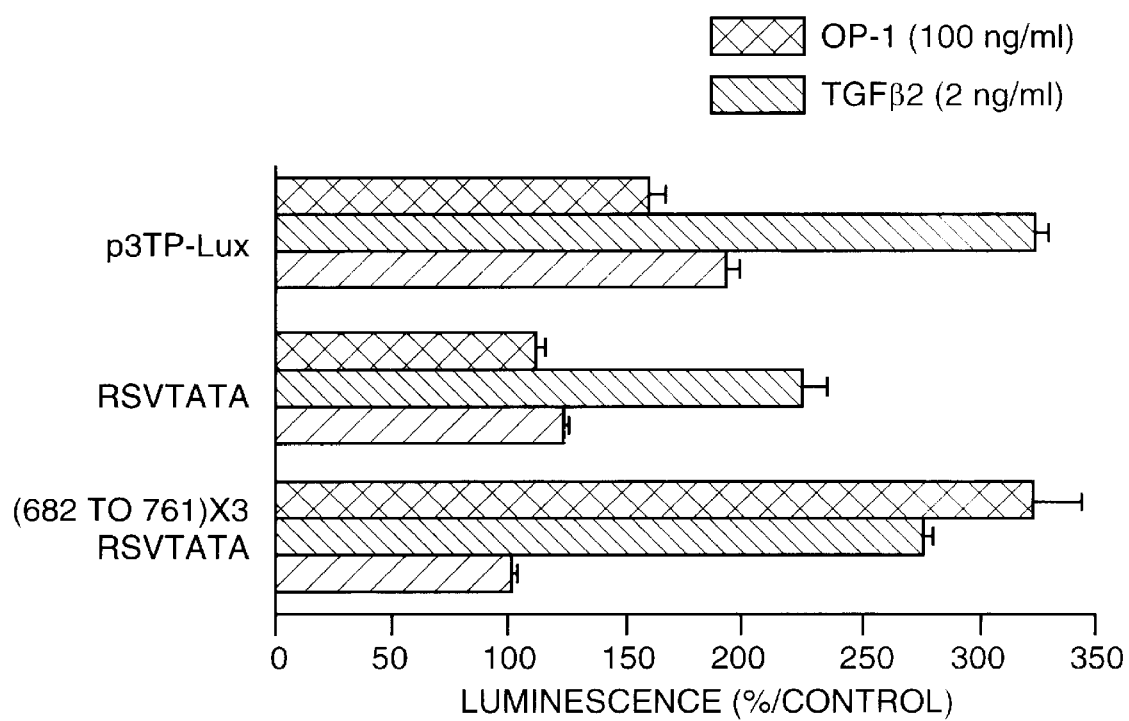
FIG. 11 is a bar graph depicting the effects of OP-1 and TGFβ on induction of a reporter gene operatively associated with a portion of the type X collagen promoter.

In contrast, TGFβ2 (2 ng/ml) had little effect on the OP-1 responsive element (nucleotides 682–761 of SEQ. ID No. 1) in the RSV promoter construct (FIG. 11), despite confirmation that the same TGFβ preparation successfully induced a TGFβ-responsive stimulation of a p3TP-Lux vector construct borne by C5.18 cells transfected according to the procedure described above.

Additional experiments were performed to further delineate features of the OP-1 responsive element within the type X collagen promoter. In particular, DNase footprinting was carried out according to established techniques, using a nucleic acid probe comprising nucleotides 682–761 of SEQ. ID No. 1. Footprinting analysis showed that a nuclear extract from C5.18 cells protected a 32 base pair region, corresponding to nucleotides 697–728 of SEQ. ID No. 1, from degradation by DNase I. The protected region comprised both a 5' AT rich sequence and a 3' sequence having similarity to a well-known AP1 binding site sequence depicted in SEQ. ID No. 2.

Next, electrophoretic gel mobility shift assays were carried out according to established technique. These assays demonstrated that exposure of C5.18 cells to OP-1 induced about a 2–3 fold increase in the amount or activity of a nuclear extract component, presumably a protein, that binds to the minimal OP-1 responsive 32 base pair fragment of the COLX promoter. Binding of the extract component produces a DNA/protein complex having retarded electrophoretic mobility relative to the mobility of the uncomplexed DNA probe. The OP-1 induced DNA protein complex could be supershifted during gel analysis when treated with an anti-c-fos antibody. This effect was observed using an antibody that binds to the conserved domain of fos gene family members (amino acids 128–152 of human c-fos; Catalog # sc-253, from Santa Cruz Biotechnology, Inc., Santa Cruz Calif.)(SEQ. ID No. 4). However, the OP-1 induced protein-DNA complex did not appear to be supershifted by antibodies specifically reactive with the related proteins c-fos, fos-B, fra-1, fra-2 or c-jun. UV cross-linking was carried out using the core 32 base pair probe sequence complexed with the nuclear extract component. Results of the crosslinking studies suggested that proteins having relative molecular masses of approximately about 55 kDa and 150 kDa cross-linked to the probe fragment comprising nucleotides 682–741 of SEQ. ID No. 1.

Figure 12:
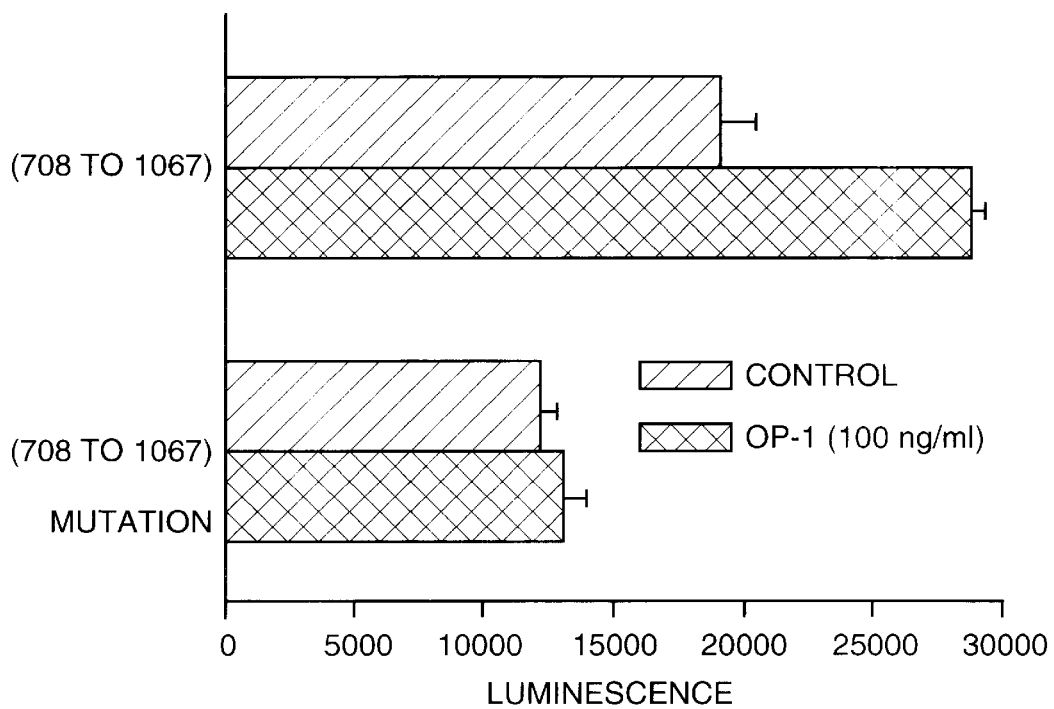
FIG. 12 is a bar graph depicting the suppressive effects of mutation of the OP-1 responsive transcription activating element on OP-1 responsiveness of a luciferase reporter gene.

Finally, site specific mutation of the aforementioned domain of the mouse type X collagen promoter that resembles an AP1 binding site sequence, SEQ. ID No. 2, i.e., TGAATCATCA at nucleotides 715–724 of SEQ. ID No. 1 to TTCCTCATCA (nucleotides 1–10 of SEQ. ID No. 3) abolished the DNA protein interaction and suppressed OP-1 responsiveness (FIG. 12).

The foregoing studies culminated in the discovery and characterization of an OP-1 responsive element in the type X collagen gene promoter. A core region (32 bp) of this OP-1 responsive element is bound by a substance present in nuclear extracts produced from OP-1 stimulated C5.18 cells. This substance has the general immunological properties of a fos family protein and may be a novel member of the fos family. Thus, the appearance and specific biological effects and/or interaction of the fos-like protein with the type X collagen promoter offers unprecedented insight into the molecular basis of tissue-specific morphogenesis. This discovery is exploited, according to the present invention, for the identification of substances which can reproduce the specific biological effects and/or intracellular events induced by OP-1.

EXAMPLE 3

Induction of Vascular Endothelial Growth Factor Expression by OP-1 in vitro and in vivo Angiogenesis is one of the earliest events in the transition from chondrogenesis to osteogenesis. Vascular endothelial growth factor (VEGF), the only secreted mitogen specific for vascular endothelial cells, has been implicated in physiological and pathological angiogenesis. Reports have indicated that VEGF expression in osteoblasts is increased by prostaglandin $E_1$ and $E_2$ and suppressed by glucocorticoids (Harada et al., (1994) *J. Clin. Invest.* 93: 2490–2496). Preliminary histochemical analysis of normal rat bone sections suggested that expression of VEGF could be localized in the hypertrophic zone of cartilage. This observation further suggested that VEGF may play a role in endochondral ossification. Thus, expression of VEGF is an indicator of endochondral bone formation induced by OP-1 and the OP-1 analogs disclosed herein, and can be measured in vivo by means of the following assay.

OP-1-charged bone specific matrix pellets (Creative BioMolecules, Inc., Hopkinton, Mass.) were implanted in 4 week old male rats according to the earlier-referenced methods described in U.S. Pat. No. 4,968,590 and Sampath et al. (1983) *Proc. Natl. Acad. Sci. USA* 80:6591–6595. Following a suitable incubation period during which endochondral bone morphogenesis commenced, RNA extracted from nodules induced by OP-1 or a candidate compound. In the case of OP-1, VEGF mRNA was highly expressed at day 11 after implantation of OP-1, subsequent to the induction of type X collagen mRNA (at day 9). In OP-1 treated animals, VEGF mRNA was associated with hypertrophic chondrocytes, consistent with its expression at the growth plate region of long bones.

OP-1 also induced VEGF MRNA in vitro in C5.18 cells. VEGF mRNA peaked at 48 h after OP-1 treatment, following the induction of cartilage markers. In contrast, OP-1 had no effect on VEGF mRNA in RCT-3 osteoblastic cells. RCT-3 is a clonal cell line derived from retrovirus-immortalized embryonic rat calvaria cells which constitutively exhibits osteoblastic characteristics, as described by Heath et al. (1989) *Endocrinology* 124:3060:3068 and incorporated herein by reference. This observation suggests that the above-described effect on VEGF production was cell type specific. That is, TGFβ1-induced VEGF niRNA in both cell lines, but with a different time course (at 12 h). These observations demonstrate that VEGF mRNA is expressed during the morphogenetic transition from cartilage to bone in vivo and that OP-1 induced VEGF mRNA in chondro-osteo progenitor cells in vitro in a cell type specific manner. Analogs are expected to have similar induction effects.

EXAMPLE 4

Induction of Osteoblast Differentiation Markers

If desired, other cellular and molecular markers for tissue-specific, OP-1 induced morphogenesis may be monitored to confirm whether a test substance that reproduces the above-described intracellular events involving the type X collagen gene promoter indeed should be viewed as an OP-1 analog. Thus, PCT US92/07432 disclosed that OP-1 preferentially induces differentiation of uncommitted mammalian progenitor cells, including embryonic mesenchymal cells and primary osteoblasts. Potential analogs of OP-1 accordingly can be screened for a similar ability to induce differentiation of primary osteoblasts, by measuring the ability of these analogs to induce specific molecular markers such as alkaline phosphatase activity, PTH-mediated cAMP production and osteocalcin expression, all of which are induced when primary osteoblasts are exposed to morphogens such as human or mouse OP-1, the Drosophila homolog thereof, 60A, or human BMP2 or the Drosophila homolog thereof, DPP, or other members of the morphogen family.

Osteoblast-enriched primary cultures from a well-characterized model mammal, such as rat, preferably are used for the present corroborative studies. Although such cultures are heterogeneous in that the individual cells thereof are at different stages of differentiation, these cultures are believed to accurately reflect the metabolism and function of osteoblasts in vivo. Unless otherwise indicated, all chemicals referenced below are standard reagents, readily available from a number of commercial sources, including Sigma Chemical, Co., St. Louis; Calbiochem, Corp., San Diego and Aldrich Chemical Co., Milwaukee.

Rat osteoblast-enriched primary cultures are prepared by sequential collagenase digestion of newborn suture-free rat calvaria (e.g., from 1–2 day-old animals, Long-Evans strain, Charles River Laboratories, Wihnington, Mass.), following standard procedures, such as are described, for example, in Wong et al. (1975) *Proc. Natl. Acad. Sci.* 72:3167–3171. Rat osteoblast single cell suspensions then are plated onto a multi-well plate (e.g., a 24 well plate) at a concentration of 50,000 osteoblasts per well in αMEM (modified Eagle's medium, Gibco, Inc., Long Island) containing 10% FBS (fetal bovine serum), L-glutamine and a standard antibiotic, such as penicillin/streptomycin. The cells are incubated for 24 hours at 37° C. If appropriate under the circumstances, the growth medium is replaced with alpha MEM containing 1% FBS and the cells incubated for an additional 24 hours.

(a) Induction of Alkaline Phosphatase Activity in Osteoblasts

The cultured cells are incubated with OP-1, a suspected OP-1 analog or a negative control, using a range of concentrations. For example, 0.1, 1.0, 10.0, 40.0 or 80.0 ng OP-1 ml medium typically are used. 72 hours after the incubation period, the cell layer is extracted with 0.5 ml of 1% Triton X-100. The resultant cell extract then is centrifuged, and 100 μl of the extract is added to 90 μl of paranitrosophenylphospate (pNPP)/glycerine mixture and incubated for 30 minutes in a 37° C. water bath and the reaction stopped with 100 μl NaOH. The samples then are analyzed with a conventional spectrophotometric plate reader (e.g., the Dynatech MR700 plate reader). Absorbance is measured at 400 nm, using p-nitrophenol as a standard to determine the presence and amount of alkaline phosphate activity. Protein concentrations are determined by the Biorad method. Alkaline phosphatase activity is calculated in units/mg protein, where 1 unit=1 nmol p-nitrophenol liberated/30 minutes at 37° C. OP-1 induces a five-fold increase in the cellular specific activity of alkaline phosphate by this method. Analogs are expected to have similar induction effects.

(b) Induction of PTH-Mediated cAMP Production in Osteoblasts

Primary cultures of mammalian, e.g., rat, osteoblasts are prepared and cultured in a multiwell plate as described above. The cultured cells then are divided into three groups: (1) wells which receive, for example, 1.0, 10.0 and 40.0 ng OP-l/ml medium); (2) wells which receive the candidate analog at various concentration ranges; and (3) a control group which receives equivalent volumes of the medium used for diluting the OP-1 or analog thereof. The plate is then incubated for another 72 hours. Thereafter, the cells are treated with medium containing 0.5% bovine serum albumin (BSA) and 1 mM 3-isobutyl-1-methylxanthine for 20 minutes followed by the addition, into half of the wells, of human recombinant parathyroid hormone (hPTH, Sigma, St. Louis) at a concentration of 200 ng/ml for 10 minutes. The cell layer then is extracted from each well with 0.5 ml of 1% Triton X-100. Cylic AMP levels then are determined using a widely available radioimmunoassay kit (e.g., Amersham, Arlington Heights, Ill.). OP-1 doubles cAMP production in the presence of PTH. Analogs are expected to have similar induction effects.

(c) Induction of Osteocalcin Production in Osteoblasts

Osteocalcin is a bone-specific protein produced by osteoblasts and secreted into the circulation. Osteocalcin plays an integral role in regulating the rate of bone mineralization in mammals. Accordingly, serum levels of osteocalcin can be monitored as an indicator of osteoblast activity and bone formation in vivo. Similarly, induction of osteocalcin synthesis in osteoblast-enriched cultures can be used to corroborate whether a suspected OP-1 analog indeed can reproduce systemic effects of OP-1 treatment.

Rat osteoblasts are prepared and cultured in a multi-well plate as above. For osteocalcin analysis, the medium contains 10% FBS, and on day 2, cells are fed with fresh medium supplemented with fresh 10 mM β-glycerophosphate (Sigma, Inc.). Beginning on day 5 and twice weekly thereafter, cells are fed with a complete mineralization medium containing all of the above components plus fresh L(+)-ascorbate, at a final concentration of 50 mg/ml medium. OP-1 or OP-1 analog then is added to the wells directly, e.g., in 50% acetonitrile (or 50% ethanol) containing 0.1% trifluoroacetic acid (TFA), at no more than 5mg OP-1/ml medium. Control wells receive solvent vehicle only. The cells then are re-fed and the conditioned medium sample diluted 1:1 in standard radioimmunoassay buffer containing standard protease inhibitors and stored at −20° C. until assayed for osteocalcin. Osteocalcin synthesis is measured by standard radioimmunoassay using a commercially available osteocalcin-specific antibody and can be confirmed by Northern blot analysis to calculate the amount of osteocalcin mRNA produced in the presence and absence of OP-1 or an OP-1 analog. OP-1 induces a dose-dependent increase in osteocalcin production (5-fold increase using 25 ng of OP-1 protein/ml), and a 20-fold increase in osteocalcin mRNA. Analogs are expected to have similar induction effects.

Mineralization is determined on long term cultures (13 day) using a modified von Kossa staining technique on fixed cell layers: Cells are fixed in fresh 4% paraformaldehyde at 23° C. for 10 min, following rinsing cold 0.9% NaCl. Fixed cells then are stained for endogenous alkaline phosphatase at pH 9.5 for 10 min, using a commercially available kit (Sigma, Inc., St. Louis, Mo.). Purple stained cells then are dehydrated with methanol and air dried. After 30 min incubation in 3% $AgNO_3$ in the dark, $H_2O$-rinsed samples are exposed for 30 sec to 254 nm UV light to develop the black silver-stained phosphate nodules. Individual mineralized foci (at least 20 mm in size) are counted under a dissecting microscope and expressed as nodules/culture. OP-1 induces a 20-fold increase in initial mineralization rate. Analogs are expected to have similar induction effects.

EXAMPLE 5

Induction of Neuronal Markers by Morphogen Analogs: CAM Expression

It is further expected that the OP-1 2nd morphogen analogs contemplated herein will induce CAM expression, particularly N-CAM expression, as part of their induction of morphogenesis. CAMs are morphoregulatory molecules identified in all tissues, especially nerve tissues, as an essential step in tissue development. N-CAMs, which comprise at least 3 isoforms (N-CAM-180, N-CAM-140 and N-CAM- 120, where "180", "140" and "120" indicate the apparent molecular weights of the isoforms as measured by polyacrylamide gel electrophoresis) are expressed at least transiently in developing tissues, and permanently in nerve tissue. Both the N-CAM-180 and N-CAM-140 isoforms are expressed in both developing and adult tissue. The N-CAM-120 isoform is found only in adult tissue. Another neural CAM is L1.

N-CAMs are particularly useful as indicators of neuronal-specific tissue morphogens or analogs thereof. They are implicated in appropriate neural development, including appropriate neurulation, neuronal migration, fasciculation, and synaptogenesis. Inhibition of N-CAM production, as by complexing the molecule with an N-CAM-specific antibody, inhibits retina organization, including retinal axon migration, and axon regeneration in the peripheral nervous system, as well as axon synapsis with target muscle cells. In addition, significant evidence indicates that physical or chemical trauma to neurons, oncogenic transformation and some genetic neurological disorders are accompanied by changes in CAM expression, which alter the adhesive or migratory behavior of these cells. Furthermore, increased N-CAM levels are reported in Huntington's disease striatum (e.g., striatal basal ganglia), and decreased adhesion is noted in Alzheimer's disease.

The OP-1 2nd morphogen analogs contemplated herein are expected to stimulate CAM production, particularly L1 and N-CAM production, including all three isoforms of the N-CAM molecule. For example, N-CAM expression can be stimulated significantly in morphogen-treated NG 108–15 cells as earlier described in U.S. Ser. No. 08/260,675, the disclosure of which is incorporated herein by reference; and in Perides et al. (1994) *J. Biol. Chem.* 269:765–770 and (1993) *J. Biol. Chem.* 268:25197–25205, the disclosures of which are also incorporated herein by reference. NG108–15 is a transformed hybrid cell line (neuroblastoma x glioma, American Type Culture Collection, Rockville, Md.) exhibiting a morphology characteristic of transformed embryonic neurons. Untreated NG108–15 cells exhibit a fibroblastic, or minimally differentiated morphology and express only the 180 and 140 isoforms of N-CAM normally associated with a developing cell. Following morphogen, e.g., OP-1, treatment, these cells exhibit a morphology characteristic of adult neurons and express enhanced levels of all three N-CAM isoforms. Using a protocol similar to that described below, treatment of NG 108–15 cells with OP-1 or morphogen analogs will to the same extent as authentic OP-1 induce L1 expression.

NG108–15 cells are cultured for 4 days in the presence of increasing concentrations of OP-1 or OP-1 analogs, and standard Western blots are then performed on whole cells extracts. N-CAM isoforms are detected with an antibody which crossreacts with all three isoforms, mAb H28.123, obtained from Sigma Chemical Co., St. Louis, the different isoforms being distinguishable by their different mobilities on an electrophoresis gel. Control NG108–15 cells (untreated) will express both the 140 kDa and the 180 kDa isoforms, but not the 120 kDa, as determined by western blot analyses using up to 100 mg of protein. Treatment of NG108–15 cells with OP-1 will result in a dose-dependent increase in the expression of the 180 kDa and 140 kDa isoforms, as well as the induction of the 120 kDa isoform. Additionally, an increase in N-CAM expression will correspond in a dose-dependent manner with the morphogen induction of multicellular aggregates. Standard immunolocalization studies performed with the mAb H28.123 on treated cells will show N-CAM cluster formation is associated with the periphery and processes of treated cells. Moreover, treatment will not inhibit cell division as determined by cell counting or $^3$H-thymidine uptake. Furthermore, these cell aggregation effects of OP-1 or OP-1 analogs on NG108–15 cells can be inhibited with anti-N-CAM antibodies or antisense N-CAM oligonucleotides. Antisense oligonucleotides can be made synthetically on a nucleotide synthesizer, using standard means known in the art. Preferably, phosphorothioate oligonucleotides ("S-oligos") are prepared, to enhance transport of the nucleotides across cell membranes. Concentrations of both N-CAM antibodies and N-CAM antisense oliognucleotides sufficient to inhibit N-CAM induction also inhibited formation of multilayered cell aggregates. Specifically, incubation of NG108–115 cells with 0.3–3 mM N-CAM antisense S-oligos, 5–500 mM unmodified N-CAM antisense oligos, or 10 mg/ml mAb H28.123 will significantly inhibit cell aggregation.

The efficacy of morphogen analog treatment on N-CAM expression in vivo may be evaluated by tissue biopsy using routine methods and immunohistochemistry by detecting N-CAM molecules with an N-CAM-specific antibody, such as mnAb H28.123. Alternatively, the level of N-CAM proteins or protein fragments present in cerebrospinal fluid or serum also may be detected to evaluate the effect of treatment. N-CAM molecules are known to slough off cell surfaces and have been detected in both serum and cerebrospinal fluid. In addition, altered levels of the soluble form of N-CAM are associated with normal pressure hydrocephalus and type II schizophrenia. N-CAM fluid levels may be detected using an N-CAM specific antibody, such as mAb H28.123 using routine immunoassay procedures.

EXAMPLE 6

General Formulation and Administration Considerations

Morphogen analogs, including OP-1 analogs, can be formulated for administration to a mammal, preferably a human in need thereof as part of a pharmaceutical composition. The composition can be administered by any suitable means, e.g., parenterally, orally or locally. Where the morphogen analog is to be administered locally, as by injection, to a desired tissue site, or systemically, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the composition preferably comprises an aqueous solution. The solution preferably is physiologically acceptable, such that administration thereof to a mammal does not adversely affect the mammal's normal electrolyte and fluid volume balance. The aqueous solution thus can comprise, e.g., normal physiologic saline (0.9% NaCl, 0.15M), pH 7–7.4.

Useful solutions for oral or parenteral systemic administration can be prepared by any of the methods well known in the pharmaceutical arts, described, for example, in *Remington's Pharmaceutical Sciences*, (Gennaro, A., ed., Mack Pub., 1990). Formulations can include, for example, polyalkylene glycols such as polyethylene glycol, oils of vegetable origin, hydrogenated naphthalenes, and the like. Formulations for direct administration, in particular, can include glycerol and other compositions of high viscosity. Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the morphogen analog in vivo.

Other potentially useful parenteral delivery systems for the present analogs can include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate or deoxycholate, or oily solutions for administration in the form of nasal drops or as a gel to be applied intranasally.

Alternatively, the morphogen analogs, including OP-1 analogs, identified as described herein may be administered orally. For example, liquid formulations of morphogen analogs can be prepared according to standard practices such as those described in *Remington's Pharmaceutical Sciences* (Gennaro, A., ed.; Mack Pub., 1990), the disclosure of which is incorporated herein by reference. Such liquid formulations can then be added to a beverage or another food supplement for administration. Oral administration can also be achieved using aerosols of these liquid formulations. Alternatively, solid formulations prepared using art-recognized emulsifiers can be fabricated into tablets, capsules or lozenges suitable for oral administration.

Optionally, the analogs can be formulated in compositions comprising means for enhancing uptake of the analog by a desired tissue. For example, tetracycline and diphosphonates (bisphosphonates) are known to bind to bone mineral, particularly at zones of bone remodeling, when they are provided systemically in a mammal. Accordingly, such components can be used to enhance delivery of the present analogs by bone tissue. Alternatively, an antibody or portion thereof that binds specifically to an accessible substance specifically associated with the desired target tissue, such as a cell surface antigen, also can be used. If desired, such specific targeting molecules can be covalently bound to the present analog e.g., by chemical crosslinking, or by using standard genetic engineering techniques to create, for example, an acid labile bond such as an Asp-Pro linkage. Useful targeting molecules can be designed, for example, according to the teachings of U.S. Pat. No. 5,091,513.

Still further, the present analogs can be administered to the mammal in need thereof either alone or in combination with another substance known to have a beneficial effect on tissue morphogenesis. Examples of such substances (herein, cofactors) include substances that promote tissue repair and regeneration and/or inhibiting inflammation. Examples of useful cofactors for stimulating bone tissue growth in osteoporotic individuals, for example, include but are not limited to, vitamin $D_3$, calcitonin, prostaglandins, parathyroid hormone, dexamethasone, estrogen and IGF-I or IGF-II. Useful cofactors for nerve tissue repair and regeneration can include nerve growth factors. Other useful cofactors include symptom-alleviating cofactors, including antiseptics, antibiotics, antiviral and antifungal agents and analgesics and anesthetics.

Analogs preferably are formulated into pharmaceutical compositions by admixture with pharmaceutically acceptable, nontoxic excipients and carriers. As noted above, such compositions can be prepared for systemic, e.g., parenteral, administration, particularly in the form of liquid solutions or suspensions; for oral administration, particularly in the form of tablets or capsules; or intranasally, particularly in the form of powders, nasal drops or aerosols. Where adhesion to a tissue surface is desired, the composition can comprise a fibrinogen-thrombin dispersant or other bioadhesive such as is disclosed, for example in PCT US91/09275, the disclosure of which is incorporated herein by reference. The composition then can be painted, sprayed or otherwise applied to the desired tissue surface.

The compositions can be formulated for parenteral or oral administration to humans or other mammals in therapeutically effective amounts, e.g., amounts which provide appropriate concentrations of the morphogen analog to target tissue for a time sufficient to induce the desired effect. Preferably, the present compositions alleviate or mitigate the mammal's need for a morphogen-associated biological response, such as maintenance of tissue-specific function or restoration of tissue-specific phenotype to senescent tissues (e.g., osteopenic bone tissue).

As will be appreciated by those skilled in the art, the concentration of the present morphogen analogs in compositions formulated for administration to mammals will vary depending upon a number of factors, including the dosage of the particular analog to be administered, the chemical characteristics (e.g., hydrophobicity) of the analog employed, the route of administration, and frequency or duration of administration. The preferred dosage of analog to be administered also is likely to depend on such variables as the type and extent of tissue loss or defect, the overall health status of the particular mammal, the relative biological efficacy or toxicity of the analog selected, the formulation of the compound, and the presence and types of excipients in the formulation.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A test cell for identifying a candidate compound that mimics OP-1 in its ability to activate transcription from an OP-1 responsive transcription activating element, said cell comprising the OP-1 responsive transcription activating element of SEQ ID NO: 1 in operative association with a reporter gene encoding a detectable gene product.

2. A method for identifying a compound that mimics OP-1 in its ability to activate transcription from an OP-1 responsive activating element, the method comprising the steps of:

(a) exposing the test cell of claim 1 to a candidate compound in vitro; and, (b) detecting expression of said detectable gene product, said expression indicating the ability of said compound to mimic OP-1 in its ability to activate transcription from an OP-1 responsive transcription activating element.

3. The method of claim 2 wherein said OP-1 responsive transcription activating element is responsive to a protein that is capable of specific binding wit a c-fos antibody.

4. The method of claim 2 wherein said reporter gene is capable of expressing luciferase.

5. The method of claim 2 wherein said OP-1 responsive transcription activating element comprises nucleotides 697–728 of SEQ ID NO: 1.

6. The method of claim 2 wherein said OP-1 responsive transcription activating element comprises nucleotides 682–696 and 729–731 of SEQ ID NO: 1.

7. The method of claim 2 wherein said OP-1 responsive transcription activating element comprises nucleotides 732–761 of SEQ ID NO: 1.

8. The method of claim 2 wherein said OP-1 responsive transcription activating element comprises nucleotides 699–731 of SEQ ID NO: 1.

9. The method of claim 2 wherein said test cell comprises an OP-1 receptor.

10. A method of determining whether a compound binds to nucleotides 682–761 of SEQ ID NO: 1, the method comprising the steps of:

(a) exposing DNA comprising nucleotides 682–761 of SEQ ID NO: 1 to a candidate compound; and, (b) detecting binding of said candidate compound to said DNA.

* * * * *

UNITED STATES PATENT AND TRADEMARK OFFICE
CERTIFICATE OF CORRECTION

PATENT NO. : 5,834,188
DATED : November 10, 1998
INVENTOR(S) : Harada et al.

It is certified that error appears in the above-identified patent and that said Letters Patent is hereby corrected as shown below:

In claim 3, line 3 please delete "wit" and add in its place --with--.

Signed and Sealed this

Third Day of August, 1999

Attest:

Attesting Officer

Q. TODD DICKINSON

Acting Commissioner of Patents and Trademarks